(12) United States Patent
Sobinov et al.

(10) Patent No.: US 11,744,720 B2
(45) Date of Patent: Sep. 5, 2023

(54) SYSTEMS AND METHODS FOR APPROXIMATING MUSCULOSKELETAL DYNAMICS

(71) Applicant: West Virginia University, Morgantown, WV (US)

(72) Inventors: Anton Sobinov, Morgantown, WV (US); Sergiy Yakovenko, Morgantown, WV (US); Valeriya Gritsenko, Morgantown, WV (US); Russell Hardesty, Eighty Four, PA (US); Matthew Boots, Morgantown, WV (US)

(73) Assignee: WEST VIRGINIA UNIVERSITY, Morgantown, WV (US)

( * ) Notice: Subject to any disclaimer, the term of this patent is extended or adjusted under 35 U.S.C. 154(b) by 602 days.

(21) Appl. No.: 16/643,163

(22) PCT Filed: Sep. 18, 2018

(86) PCT No.: PCT/US2018/051575
§ 371 (c)(1),
(2) Date: Feb. 28, 2020

(87) PCT Pub. No.: WO2019/056008
PCT Pub. Date: Mar. 21, 2019

(65) Prior Publication Data
US 2020/0265943 A1     Aug. 20, 2020

Related U.S. Application Data

(60) Provisional application No. 62/559,711, filed on Sep. 18, 2017.

(51) Int. Cl.
*A61F 2/70*      (2006.01)
*A61F 2/08*      (2006.01)
(Continued)

(52) U.S. Cl.
CPC .............. *A61F 2/72* (2013.01); *A61B 5/1107* (2013.01); *A61B 5/4519* (2013.01); *A61F 2/582* (2013.01);
(Continued)

(58) Field of Classification Search
None
See application file for complete search history.

(56) References Cited

U.S. PATENT DOCUMENTS

2013/0310979 A1*   11/2013   Herr .................... B62D 57/032
                                                       700/258
2014/0364723 A1    12/2014   Meyer et al.
(Continued)

FOREIGN PATENT DOCUMENTS

WO      2019056008 A1     3/2019

OTHER PUBLICATIONS

Chadwick, et al., "A Real-Time 3-D Musculoskeletal Model for Dynamic Simulation of Arm Movements", IEEE Transactions on Biomedical Engineering, Sep. 26, 2008.
(Continued)

*Primary Examiner* — David H Willse
(74) *Attorney, Agent, or Firm* — Thomas | Horstemeyer, LLP

(57) ABSTRACT

An approximation method and system are provided for more quickly controlling a prosthetic or other device by reducing computational processing time in a muscle model that can be used to control the prosthetic. For a given muscle, the approximation method can quickly compute polynomial structures for a muscle length and for each associated moment arms, which may be used to generate a torque for a joint position of a physics model. The physics model, in turn, produces a next joint position and velocity data for driving a prosthetic. The approximation method expands the (Continued)

polynomial structures as long as expansion is possible and sufficiently beneficial. The computations can be performed quickly by expanding the polynomial structures in a way that constrains the muscle length polynomial to the moment arm polynomial structures, and vice versa.

24 Claims, 11 Drawing Sheets

(51) Int. Cl.
*A61B 5/11* (2006.01)
*A61F 2/72* (2006.01)
*A61F 2/58* (2006.01)
*G06F 3/01* (2006.01)
*G16H 30/20* (2018.01)
*B25J 9/10* (2006.01)
*A61B 5/00* (2006.01)
*A61F 2/68* (2006.01)
*A61B 5/389* (2021.01)
*A61F 2/50* (2006.01)

(52) U.S. Cl.
CPC .............. *A61F 2/70* (2013.01); *B25J 9/1075* (2013.01); *G06F 3/011* (2013.01); *G06F 3/015* (2013.01); *G16H 30/20* (2018.01); *A61B 5/389* (2021.01); *A61F 2002/0894* (2013.01); *A61F 2002/5066* (2013.01); *A61F 2002/6827* (2013.01); *A61F 2002/6872* (2013.01); *A61F 2002/704* (2013.01); *A61H 2230/605* (2013.01); *A63B 2230/605* (2013.01)

(56) References Cited

U.S. PATENT DOCUMENTS

2016/0207201 A1 7/2016 Herr et al.
2017/0266019 A1 9/2017 Farina et al.
2017/0360578 A1 12/2017 Shin et al.

OTHER PUBLICATIONS

Kurse, et al., "Extrapolatable Analytical Functions for Tendon Excersions and Moment Arms from Sparse Datasets", Transactions on Biomedical Engineering, Mar. 5, 2012.
International Search Report in co-pending, related PCT Application No. PCT/US2018/051575, dated Jan. 4, 2019.
International Search Report and Written Opinion dated Mar. 16, 2021 for PCT Patent Application No. PCT/US20/66266.
Delp, Scott L., et al. "OpenSim: open-source software to create and analyze dynamic simulations of movement." IEEE transactions on biomedical engineering 54.11 (2007): 1940-1950.
Menegaldo, Luciano Luporini; et al. "A 'cheap'optimal control approach to estimate muscle forces in musculoskeletal systems." Journal of biomechanics 39.10 (2006): 1787-1795.
Sartori, Massimo, et al. "Estimation of musculotendon kinematics in large musculoskeletal models using multidimensional B-splines." Journal of biomechanics 45.3 (2012): 595-601.

* cited by examiner

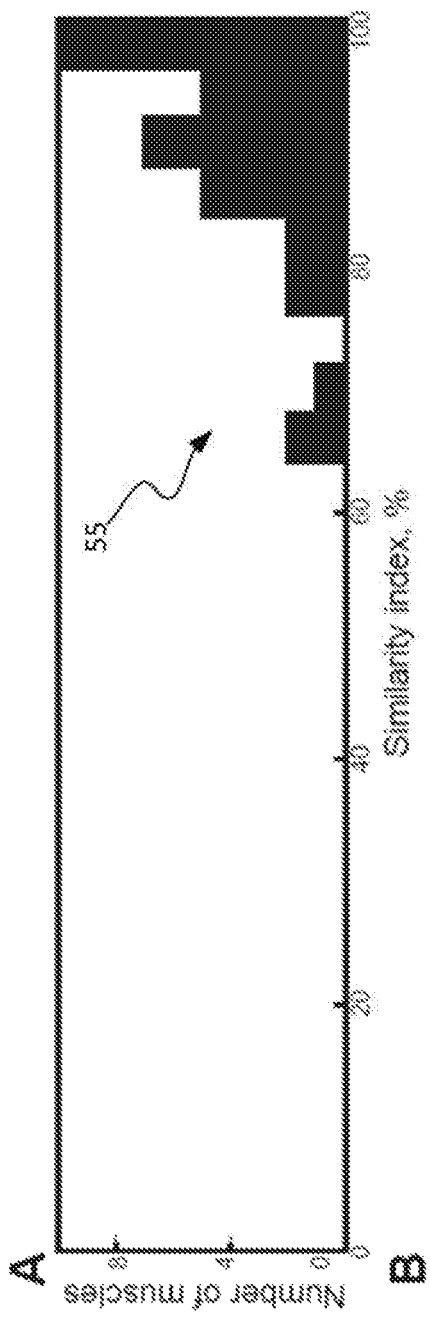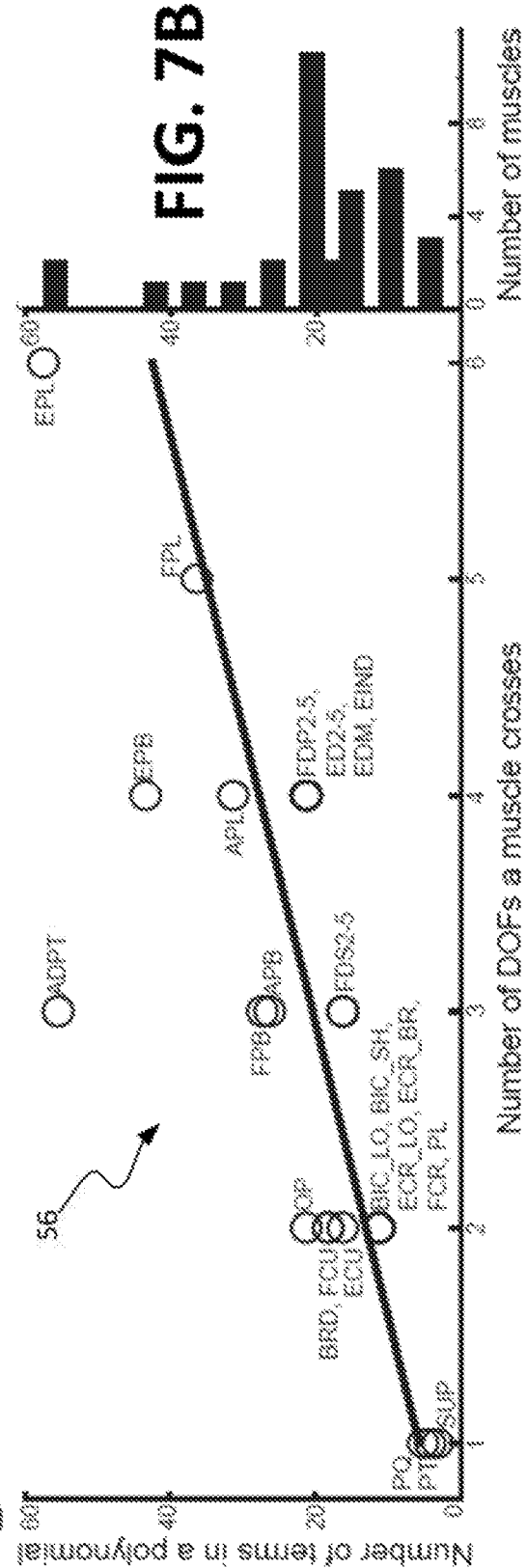

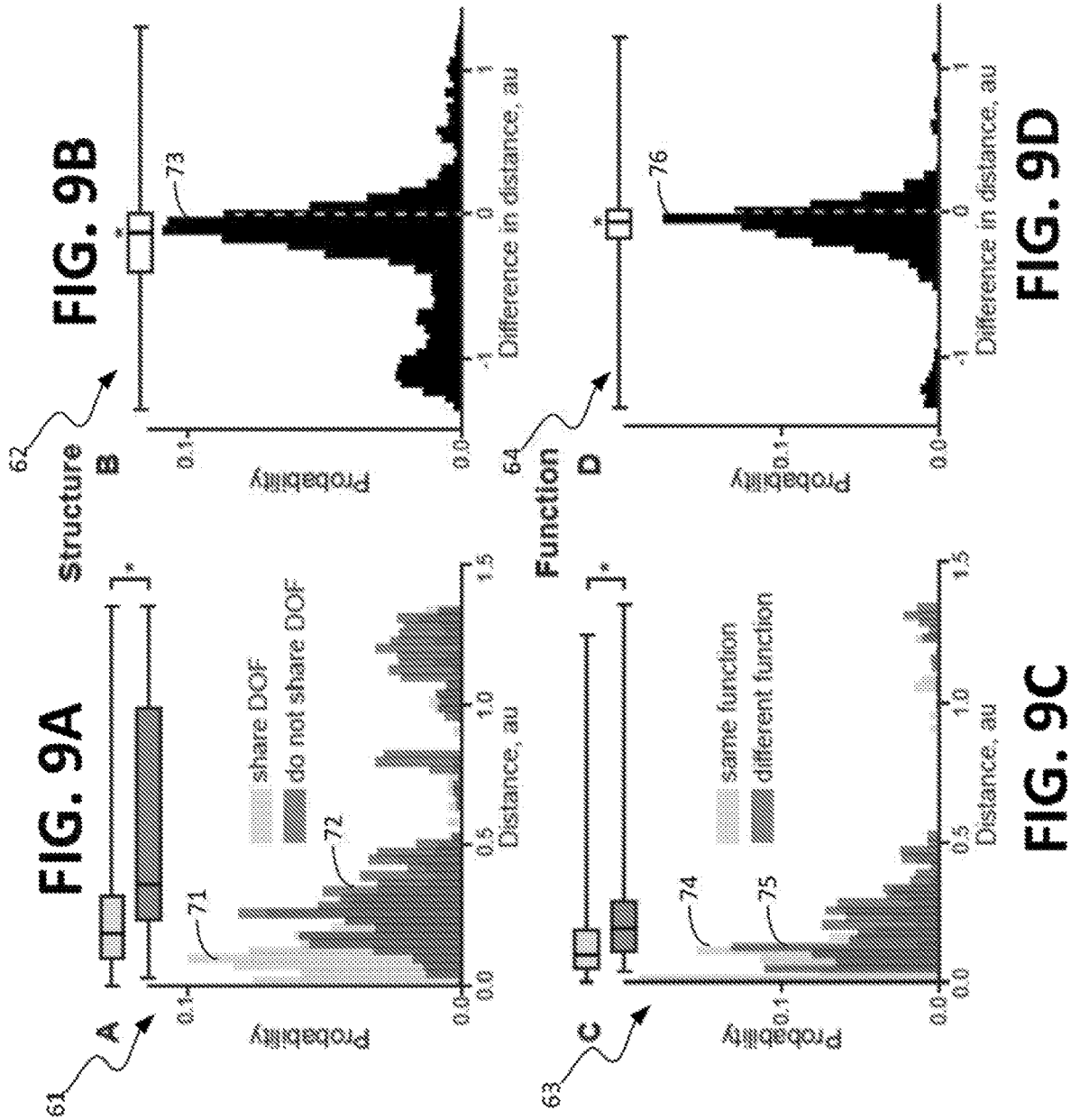

SYSTEMS AND METHODS FOR APPROXIMATING MUSCULOSKELETAL DYNAMICS

CROSS-REFERENCE TO RELATED APPLICATIONS

This application is the 35 U.S.C. 371 national stage application of PCT Application No. PCT/US2018/051575, filed Sep. 18, 2018 entitled "SYSTEMS AND METHODS OF APPROXIMATING MUSCULOSKELETAL DYNAMICS" which claims priority to and the benefit of the filing date of a U.S. provisional application having Ser. No. 62/559,711, filed on Sep. 18, 2017, entitled "APPROXIMATION OF COMPLEX MUSCULOSKELETAL DYNAMICS," which applications are hereby incorporated by reference herein in their entireties.

GOVERNMENT SUPPORT

This invention was made with support from the Defense Advanced Research Projects Agency (DARPA) of the United States Department of Defense under Cooperative Agreement Number W911NF-15-2-0016. The U.S. Government has certain rights in this invention.

FIELD OF THE INVENTION

The present invention generally relates to prosthetics, and more particularly, to systems and methods for controlling prosthetics, for example, artificial prosthetic arms and legs.

BACKGROUND OF THE INVENTION

Currently, prosthetics are limited in use and function due to their lack of incorporation of human generated signals (muscle activation and sensory information, for example). Instead, most prosthetics are statically fixed in one posture, preventing real world interactions between the prosthetic limb and the environment. A limiting factor in the development of better, more interactive prosthetic devices is the lack of real-time software that can calculate the interactions between bones and muscles. The development of such software is difficult because the musculoskeletal interactions are extremely complex and hard to describe, as they span multiple dimensions. Simulations of this dynamic system are computationally costly for applications that require real-time full limb movement. This type of solution is critical to developing a prosthetic that can move and act naturally, using the recipient's biological signals, such as muscle activity and simulations of dynamic interactions between muscles and bones.

The predominant approach is to simulate musculoskeletal dynamics using the detailed numerical of physical interactions by, for example, dynamically modeling the musculoskeletal anatomy and physiology in OpenSim (Standford, Calif.), which is open source software that can be used to create and analyze dynamic simulations of movement. However, this method is computationally costly, and it requires a dedicated software application to model and to update these geometric transformations. However, several groups have proposed simplifications to these calculations by using global approximations to improve simulation speeds. The global approximations in the form of inverse solutions have been successfully implemented to estimate muscle forces for problems that do not require a muscle model. The joint dynamics were described using inverse solutions, but without the muscle level description, which is the main limitation.

More recently, B-splines were used as an approximation method to calculate the musculotendon length and moment arms as functions of joint angles. This method improved precision of these calculations and enabled the implementation of muscle modeling, but the number of best-fit parameters increased exponentially with the number of vertices and degrees of freedom (DOFs) required for different muscles.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 7A illustrates a graph of similarity index (SI) between polynomials composed with and without the differential relationship between length and moment arms of each muscle, which illustrates that the compositions are similar.

FIG. 7B illustrates a graph of the number of joints the muscle spans vs. the number of terms in the approximating polynomials, which demonstrates that the number of terms increases with the number of joints the muscle spans.

FIG. 9A is a graph showing two probability density distributions of muscle vector distances for muscles with and without shared anatomical DOFs. The asterisks indicate $p<10^{-8}$ in statistical comparisons with $\alpha=0.05$.

FIG. 9B is a graph showing the difference between the distributions in FIG. 9A. The asterisk indicate $p<10^{-8}$ in a statistical comparison to zero with $\alpha=0.05$.

FIG. 9C is a graph showing two probability density distributions of muscle vector distances for muscles sharing spanning at least one the same DOF and belonging to two different functional groups, e.g., flexors and extensors.

FIG. 9D is a graph showing the difference between the distributions in FIG. 9C.

DETAILED DESCRIPTION

Figure 1:
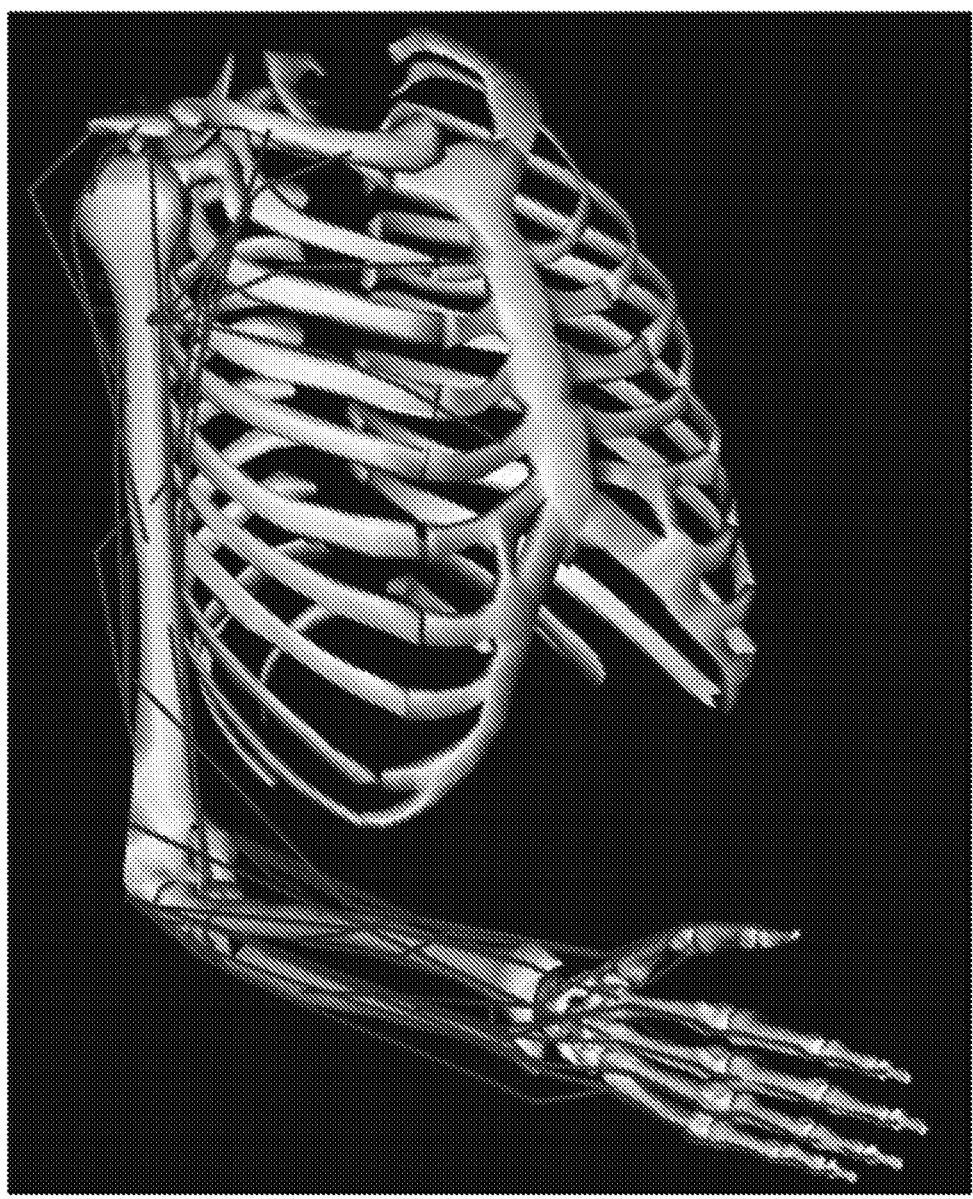
FIG. 1 is an OpenSim model of an upper limb of a human arm having various musculotendon actuators.

In accordance with representative embodiments of the present disclosure, the approximation method includes the steps of acquiring or receiving an input dataset associated with muscle lengths and moment arms for a plurality of physiological postures of a body limb, preselecting respective polynomials that approximate the muscle moment arms and lengths, generating respective lists of one or more candidates for expanding each respective polynomial, selecting a respective candidate for expanding each polynomial based on respective estimates of which of the candidates is the most suitable candidate, expanding the respective polynomials by the respective selected candidates, determining whether further expansion of the polynomials is possible and would be sufficiently beneficial to warrant expansion. If so, the process returns to the step of generating respective lists of candidates for expansion followed by the step of selecting the respective suitable candidates. If not, the musculoskeletal dynamics of the limb are estimated based on the latest structure of the polynomials.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

The term "memory" or "memory device", as those terms are used herein, are intended to denote a non-transitory computer-readable storage medium that is capable of storing computer instructions, or computer code, for execution by one or more processors. References herein to "memory" or "memory device" should be interpreted as one or more memories or memory devices. The memory may, for example, be multiple memories within the same computer system. The memory may also be multiple memories distributed amongst multiple computer systems or computing devices.

A "processor", as that term is used herein encompasses an electronic component that is able to execute a computer program or executable computer instructions. References herein to a computer comprising "a processor" should be interpreted as a computer having one or more processors or processing cores. The processor may for instance be a multi-core processor. A processor may also refer to a collection of processors within a single computer system or distributed amongst multiple computer systems. The term "computer" should also be interpreted as possibly referring to a collection or network of computers or computing devices, each comprising a processor or processors. Instructions of a computer program can be performed by multiple processors that may be within the same computer or that may be distributed across multiple computers.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

For purposes of demonstrating the inventive principles and concepts, the systems and methods will be described with reference to approximating complex musculoskeletal dynamics of the right arm and hand of a human being. However, persons of skill in the art will understand, in view of the description provided herein, that the systems and methods described herein can be used to approximate the musculoskeletal dynamics of any anatomical feature.

FIG. 1 is an OpenSim model 1 of a human right arm and hand showing the geometry of muscle paths as straight and curved lines over the skeletal structure for the displayed posture. The model 1, which is defined by the values shown in Tables 1 and 2 below for the limb shown in FIG. 1, is a known model that was previously developed to capture the relationship between muscle lengths and moment arms in all physiological postures. The model 1 contains a plurality of muscles described with a plurality of musculotendon actuators. The values for the corresponding kinematic variables were obtained on a uniform grid with nine points per DOF, resulting in the domain size of $9^d$ data points per muscle, where d is the number of DOFs that a muscle crosses. For example, since extensor carpi ulnaris muscle spans two DOFs (wrist flexion-extension and pronation-supination) its moment arms and muscle lengths were sampled in $9^2=81$ positions.

TABLE 1

| id | Name | Range, rad | Description |
|---|---|---|---|
| 1 | ra_wr_s_p | −1.5708 1.5708 | wrist pronation/supination motion |
| 2 | ra_wr_e_f | −1.2217 1.2217 | wrist flexion/extension motion |
| 3 | ra_cmc1_f_e | 0 0.8727 | thumb proximal flexion/extension motion |
| 4 | ra_cmc1_ad_ab | 0 0.8727 | thumb proximal abduction/adduction motion |
| 5 | ra_mcp1_f_e | −0.7854 0 | thumb central flexion/extension motion |
| 6 | ra_ip1_f_e | −1.5708 0 | thumb distal flexion/extension motion |
| 7 | ra_mcp2_e_f | 0 1.5708 | index proximal flexion/extension motion |
| 8 | ra_pip2_e_f | 0 2.0944 | index central flexion/extension motion |
| 9 | ra_dip2_e_f | 0 1.5708 | index distal flexion/extension motion |
| 10 | ra_mcp3_e_f | 0 1.5708 | middle proximal flexion/extension motion |
| 11 | ra_pip3_e_f | 0 2.0944 | middle central flexion/extension motion |
| 12 | ra_dip3_e_f | 0 1.5708 | middle distal flexion/extension motion |
| 13 | ra_mcp4_e_f | 0 1.5708 | ring proximal flexion/extension motion |
| 14 | ra_pip4_e_f | 0 2.0944 | ring central flexion/extension motion |
| 15 | ra_dip4_e_f | 0 1.5708 | ring distal flexion/extension motion |
| 16 | ra_mcp5_e_f | 0 1.5708 | pinky proximal flexion/extension motion |
| 17 | ra_pip5_e_f | 0 2.0944 | pinky central flexion/extension motion |
| 18 | ra_dip5_e_f | 0 1.5708 | pinky distal flexion/extension motion |
| 19 | ra_el_e_f | 0 2.2689 | elbow flexion/extension motion |

The list of simulated DOFs. The last two suffixes separated by underscores indicate the direction of the motion, e.g., "s_p" indicates the motion from supinated to pronated posture.

TABLE 2

| id | Name | Full name | DOFs |
|---|---|---|---|
| 1 | BIC_LO | Biceps brachii long head | 19 1 |
| 2 | BIC_SH | Biceps brachii short head | 19 1 |
| 3 | BRR | Brachioradialis | 19 1 |
| 4 | SUP | Supinator | 1 |
| 5 | PT | Pronator teres | 1 |
| 6 | PQ | Pronator quadratus | 1 |
| 7 | ECR_LO | Extensor carpi radialis longus | 1 2 |
| 8 | ECR_BR | Extensor carpi radialis brevis | 1 2 |
| 9 | ECU | Extensor carpi ulnaris | 1 2 |
| 10 | FCR | Flexor carpi radialis | 1 2 |
| 11 | FCU | Flexor carpi ulnaris | 1 2 |
| 12 | PL | Palmaris longus | 1 2 |
| 13 | FDS5 | Flexor digitorum superficialis (pinky finger) | 2 16 17 |
| 14 | FDS4 | Flexor digitorum superficialis (ring finger) | 2 13 14 |
| 15 | FDS3 | Flexor digitorum superficialis (middle finger) | 2 10 11 |
| 16 | FDS2 | Flexor digitorum superficialis (index finger) | 2 7 8 |
| 17 | FDP5 | Flexor digitorum profundus (pinky finger) | 2 16 17 18 |
| 18 | FDP4 | Flexor digitorum profundus (ring finger) | 2 13 14 15 |
| 19 | FDP3 | Flexor digitorum profundus (middle finger) | 2 10 11 12 |
| 20 | FDP2 | Flexor digitorum profundus (index finger) | 2 7 8 9 |
| 21 | EDM | Extensor digiti minimi | 2 16 17 18 |
| 22 | ED5 | Extensor digitorum (pinky finger) | 2 16 17 18 |
| 23 | ED4 | Extensor digitorum (ring finger) | 2 13 14 15 |
| 24 | ED3 | Extensor digitorum (middle finger) | 2 10 11 12 |
| 25 | ED2 | Extensor digitorum (index finger) | 2 7 8 9 |
| 26 | EIND | Extensor indicts | 2 7 8 9 |
| 27 | EPL | Extensor pollicis longus | 1 2 4 3 5 6 |
| 28 | EPB | Extensor pollicis brevis | 2 4 3 5 |
| 29 | FPB | Flexor pollicis brevis | 4 3 5 |
| 30 | FPL | Flexor pollicis longus | 2 4 3 5 6 |
| 31 | APL | Abductor pollicis longus | 1 2 4 3 |
| 32 | OP | Opponens pollicis | 4 3 |
| 33 | APB | Abductor pollicis brevis | 4 3 5 |
| 34 | ADPT | Adductor pollicis transversus | 4 3 5 |

The list of simulated muscles. The list of DOFs that each muscle spans is shown with the list of id values from the previous table.

To compare quality for the approximations with different known methods that are described below, a dataset (total 1,023,474 points) was used that combined the points used for the creation of the models (675,162, grid of 9 points per DOF per muscle), and an additional test dataset between the fitting data (348,312, grid of 8 points per DOF per muscle).

The aforementioned preselected polynomials that approximate the muscle moment arms and lengths have the polynomial structure given by Equation 1:

$$f(x) = a + \Sigma_p^{\rho} \Sigma_{i_1 \leq i_2 \leq \ldots \leq i_p}^{d} M_{i_1, i_2, \ldots, i_p} \Pi_j^p x_{i_j} \quad \text{Equation 1}$$

where a is an intercept, ρ is the user-selected maximum of polynomial power, d is the number of DOFs, $x = (x_1, \ldots, x_d)^T$ is the state vector for each DOF, M is the multidimensional matrix of polynomial terms, and indices in sums and product start at 1. The non-zero values of M and the intercept define the polynomial structure. For example, extensor carpi ulnaris moment arms are described by (a, $M_0$, $M_1$, $M_{00}$, $M_{01}$, $M_{11}$, $M_{000}$, $M_{001}$, $M_{011}$, $M_{111}$) around elbow flexion-extension, and (a, $M_0$, $M_{00}$, $M_{01}$, $M_{11}$, $M_{000}$, $M_{001}$, $M_{011}$, $M_{111}$) around wrist pronation-supination, where index 0 is pronation-supination and 1 is flexion-extension. Values for these non-zero elements were obtained using a known linear pseudoinverse, such as, for example, the Moore-Penrose inverse. As will be described below in more detail, in accordance with a preferred embodiment, terms are added to the polynomial structure given by Equation 1 as needed to improve the approximation, but in a way that greatly reduces the amount of time and resources required to perform the approximation computations.

Figures 2A, 2B:
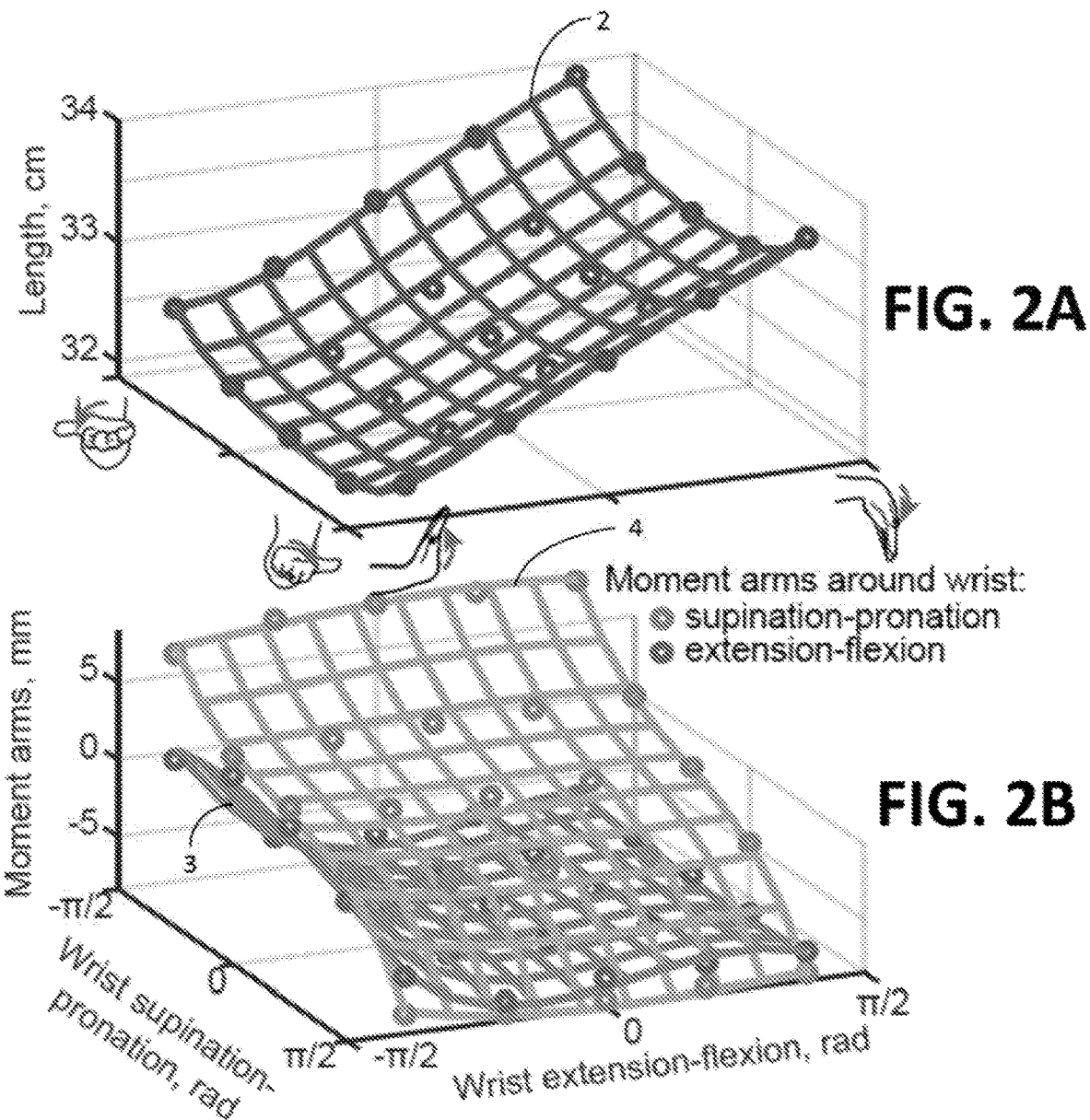
FIGS. 2A and 2B are plots of kinematic variables in terms of muscle length versus (vs.) radians and moment arm vs. radians, respectively, for the extensor carpi ulnaris muscle in different positions of wrist extension-flexion (e-f) and supination-pronation (s-p) degrees of freedom (DOFs).

FIGS. 2A and 2B contain plots 2-4 of kinematic variables in terms of muscle length versus (vs.) radians and moment arm vs. radians, respectively, for the extensor carpi ulnaris muscle in different positions of wrist extension-flexion (e-f) and supination-pronation (s-p) DOFs. The points in FIGS. 2A and 2B correspond to the approximated data. The accuracy of polynomial fit generally increases as the number of terms in the polynomial structure increases. A list of polynomials that contain one more term than a preselected polynomial P(x) will be referred to herein as the list of potential candidates Ψ(P(x)) for expansion of the preselected polynomial. Each element of this list is a polynomial with the structure of P(x), but having one additional term that is present in the full polynomial of the correct power and dimensionality, but lacking in P(x). The number of elements in the list equals the number of elements that are present in the full polynomial but lacking in P(x). For example, let P(x) be a two-dimensional polynomial with structure (a, $M_0$, $M_{00}$), full 2-dimensional polynomial of power 2 has a structure (a, $M_0$, $M_1$, $M_{00}$, $M_{01}$, $M_{11}$). Then the list of potential candidates is: Ψ(P(x))=[(a, $M_0$, $M_1$, $M_{00}$); (a, $M_0$, $M_{00}$, $M_{01}$); (a, $M_0$, $M_{00}$, $M_{11}$)].

Figure 3:
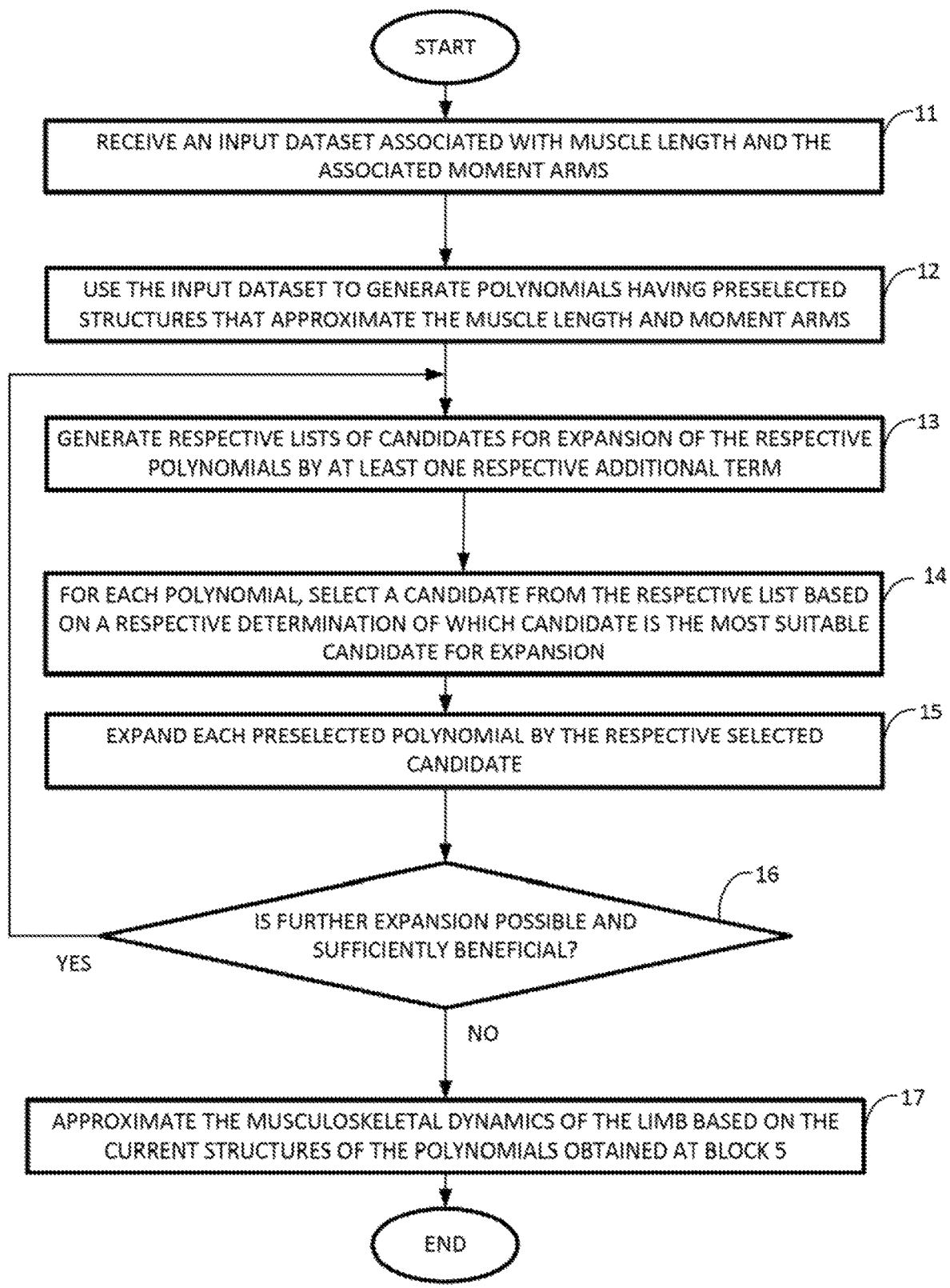
FIG. 3 is a flow diagram representing the approximation method performed by a processor in accordance with a representative embodiment.

FIG. 3 is a flow diagram representing the approximation method performed by a processor in accordance with a representative embodiment. For ease of discussion, the approximation method represented by the flow diagram will be described with reference to polynomials associated with a muscle length and the moment arms of a single muscle for a plurality of limb postures. For this example, it will be assumed that there are two moment arms associated with the muscle. In other words, for this example, the muscle crosses two DOFs. Therefore, the method will use a first polynomial associated with the muscle length and first and second polynomials associated with first and second moment arms, respectively. It should be understood, however, that for a given limb being modeled, the method represented by the flow diagram may be performed for one or more muscles of the limb, for one or more limb postures, for one or more muscle lengths and for the associated moment arms, depending on the application. For example, it may not be necessary to perform the method for all muscles of the right arm and the associated muscle lengths and moment arms if the model is being used to control a right hand prosthetic. The range of simulation can be represented by a single posture or by the full range of postures.

With reference to FIG. 3, an input dataset associated with the muscle length and the two moment arms is received in the processor, as indicated by block 11. The input dataset is used to generate a first polynomial having a preselected structure that approximates the muscle length and first and second polynomials associated with the corresponding moment arms, as indicated by block 12. The preselected structure is an empty list in the beginning, and a polynomial starts without any terms. For each of the polynomials, a list of one or more candidates for expanding the polynomial structure by at least one additional term is generated, as indicated by block 13. For each of the polynomials, one of the candidates on the respective list is selected for expanding the respective polynomial structure based on a respective determination of which of the candidates on the respective list is the most suitable candidate, as indicated by block 14. Each polynomial structure is then expanded by the respective selected candidate, as indicated by block 15. For each expanded polynomial, a determination is made as to whether further expansion of the polynomial structure is possible, and if so, whether expansion would be sufficiently beneficial to warrant expansion, as indicated by block 16. If so, the process returns to block 13. If not, the musculoskeletal dynamics of the limb are estimated based on the current structures of the polynomials obtained at block 15, as indicated by block 17.

In accordance with a preferred embodiment, the approximation method is constrained by a known relationship that exists between muscle length and the associated moment arms, which is given below by Equation 2. Moment arms can be estimated as a partial differential of the associated muscle length in local coordinates as:

$$M_i(x) = \frac{\delta L(x)}{\delta x_i} \quad \text{Equation 2}$$

where i is the index of a DOF actuated by the muscle, $x_i$ is the coordinate of DOF i, $M_i(x)$ is the posture-dependent function of the muscle's moment arm around DOF i, L(x) is the function of muscle length. In accordance with a preferred embodiment, the relationship expressed by Equation 2 is used to constrain the polynomial terms used in the approximation functions for the kinematic variables ($P_L(x), \{P_{Mi}(x)\}$), as will now be described with reference to FIG. 4.

Figure 4:
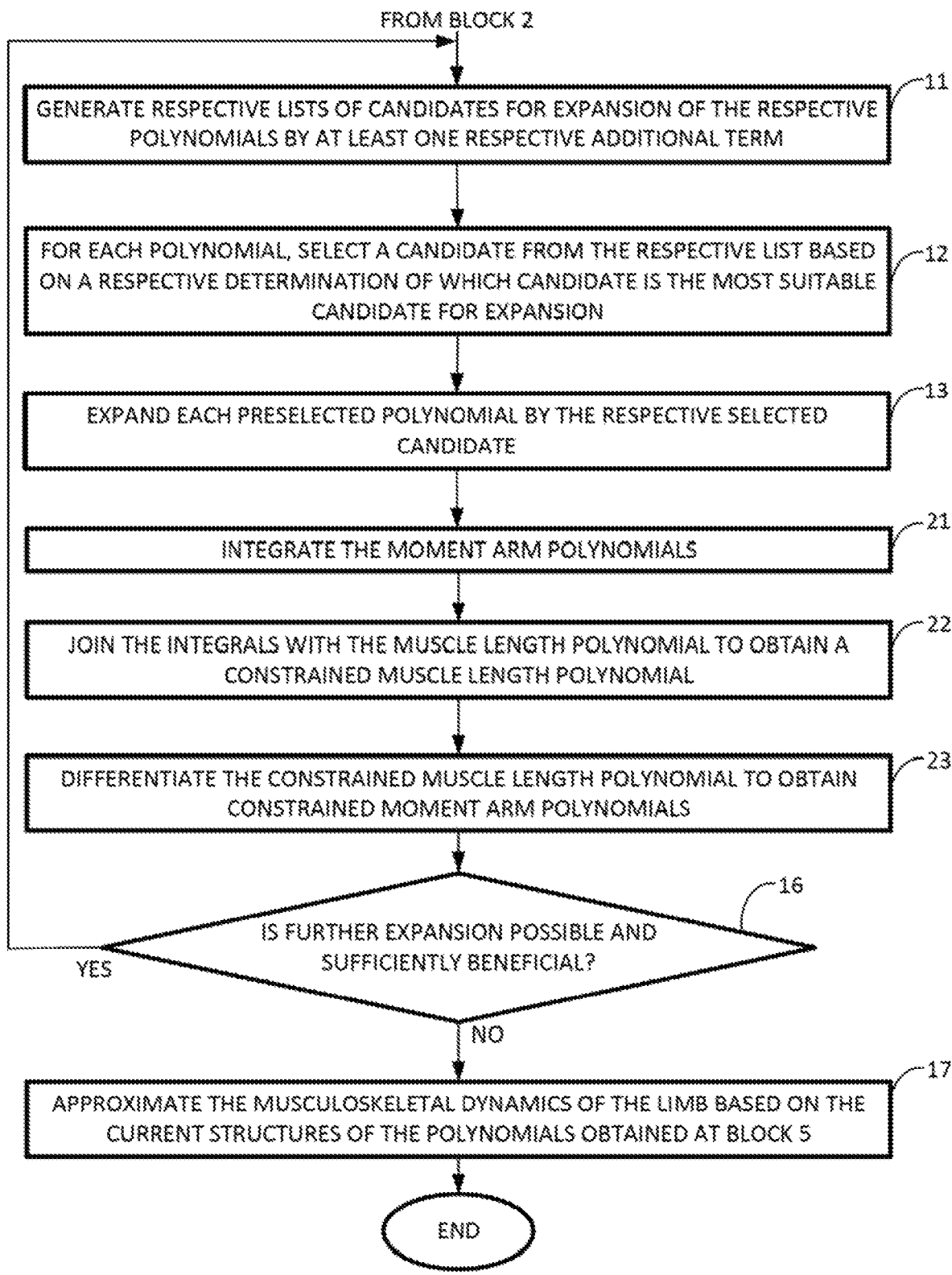
FIG. 4 is a flow diagram representing the approximation method in accordance with a preferred embodiment in which the muscle length polynomial and the moment arm polynomials are constrained by a relationship that exists between muscle length and associated moment arms.

FIG. 4 is a flow diagram representing the approximation method in accordance with the preferred embodiment in which the muscle length polynomial and the moment arm polynomials are constrained by the relationship expressed by Eq. 2. The approximation method is identical to the approximation method represented by the flow diagram shown in FIG. 3 except that additional steps represented by blocks 21-23 in FIG. 4 are performed to constrain the polynomials in accordance with the relationship expressed by Eq. 2. As will be described below in more detail, constraining the polynomials allows the polynomial structures to be optimized, or at least improved, at very high speed, which greatly reduces the overall amount of time that is required to perform the computations.

With reference to FIG. 4, after each polynomial structure has been expanded by the respective selected candidate at the step represented by block 15, the moment arm polynomials are integrated, as indicated by block 21. This process can be expressed as: calculate $\{P_{Li} = \int P_{Mi} dx_i\}$. The integrals are then joined with the expanded muscle length polynomial, as indicated by block 22. This process can be expressed as: $P_L$ or $P_{Li}$: $L = P_L \cup (\cup_i P_{Li})$. The step of joining the integrals with the expanded muscle length polynomial results in a new muscle length polynomial having each term that is present in the integrals and in the expanded muscle length polynomial and having coefficients for the terms that are recalculated using the input dataset obtained at block 11 that the approximation method is attempting to fit. The new muscle length polynomial, L(x), obtained at the step represented by block 22 is then differentiated at the step represented by block 23 to produce new moment arm polynomials, $M_i(x)$. This process can be expressed as:

$$\left\{M_i(x) = \frac{dL(x)}{dx_i}\right\}.$$

For example, let $x=(x_1,x_2)$, $P_L=2x_1x_2^2$, $P_{M1}==3x_1^3+2$, $P_{M2}=5x_1x_2$. Then $P_{L1}=x_1^4+2x_1+$const, $P_{L2}=2.5x_1x_2^2$ const. And the resulting polynomial functions adhering to Eq. 2 are: $L=C_0+C_1x_1x_2^2+C_2x_1^4+C_3x_1$, $M_1=C_4x_2^2+C_5x_1^3+C_6$, $M_2=C_7x_1x_2$, where coefficients $C_{0-7}$ are calculated using the original dataset and a linear pseudoinverse. Similarly, it can be easily described using structures: $P_L$: ($M_{122}$), $P_{M1}$: (a, $M_{111}$) $P_{M2}$: ($M_{12}$); therefore $P_{L1}$: (a, $M_1$, $M_{1111}$), $P_{M2}$: (a, $M_{122}$); and so L: (a, $M_1$, $M_{122}$, $M_{1111}$), $M_1$: (a, $M_{22}$, $M_{111}$), $M_2$: ($M_{12}$).

The process then continues to the step represented by block 16 described above with reference to FIG. 3. Muscle paths vary greatly in their complexity, from the simplest, which barely change with posture and can be approximated with a constant, to very complex that require many polynomial terms. To choose the best polynomial structure, one ought to test each one and choose the best. The number of possible structures representing a muscle across physiological postures grows exponentially with the number of DOFs that a muscle crosses. In accordance with a preferred embodiment, the steps represented by blocks 14-16 comprise an optimization algorithm that is based on forward stepwise regression and that gradually expands the polynomial structures by adding more terms as long as a determination is made at block 16 that the information tradeoff is beneficial, and it is possible to expand the polynomial structures. The information tradeoff is expressed as the corrected Akaike Information Criterion (AICc, Equation 3), which is a correction of Akaike Information Criterion for a finite sample size to avoid overfitting. The lower new value of AICc corresponds to the beneficial choice where a new polynomial approximates the data with higher precision using less variables, higher precision and using the same number of variables, the same precision using less variables, and in some other more complex cases. In accordance with this embodiment, the optimization algorithm compares the models corresponding to the polynomials of the listed expanded potential candidates to one another and chooses the best (the one with the lowest AICc). That model, it turn, is compared to the model created in the previous iteration.

$$AICc(f) = AIC(f) + \frac{2k(k+1)}{N-k-1} = 2k - 2\ln(L) + \frac{2k(k+1)}{N-k-1} \quad \text{Equation 3}$$

where f is the approximation function, AIC is the Akaike Information Criterion, k is the number of parameters in the model, N is the number of data points, and L is the maximum likelihood of the polynomial representing this dataset.

For demonstrative purposes, the AIC calculation assumes a normal distribution of residuals and is based on normalized root means squared $$\left(RMS = \left(\frac{RSS}{N}\right)^{0.5}\right); \; AICc(f) = 2k + 2N\ln(RMS) + \frac{2k(k+1)}{N-k-1} \quad \text{Equation 4}$$

The kinematic variables are normalized to preserve consistency in term N·ln(RMS) across DOFs. Muscle lengths are normalized to the range of motion, and moment arms are normalized to the maximum magnitude across postures. Go to step 12. If all functions cannot expand anymore (length of Ψ(F) is zero) or if the AICc did not improve in the current iteration, the approximation performs the step represented by block 17 and finishes.

Figure 5:
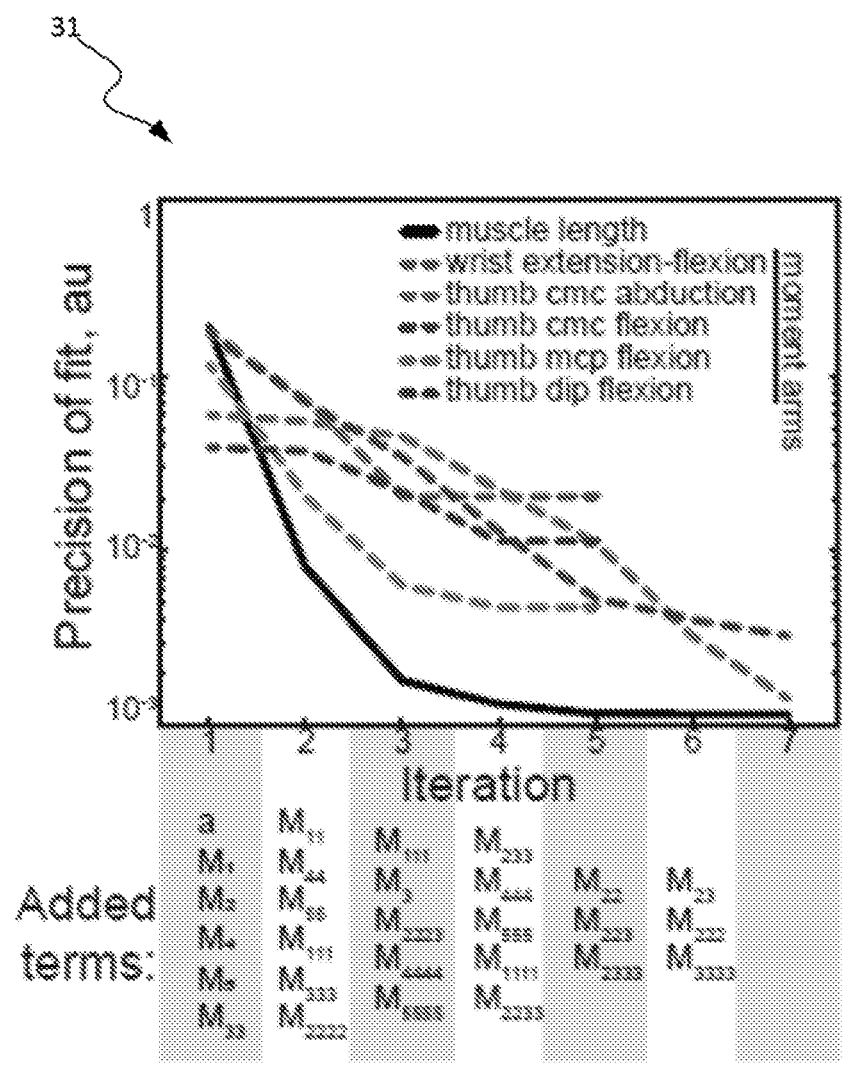
FIG. 5 is a graph showing iteration of the approximation method represented by the flow diagram of FIG. 4 vs. the precision of the fit obtained by the method.

FIG. 5 is a graph 31 showing iteration of the approximation method represented by the flow diagram of FIG. 4 vs. the precision of the fit obtained by the method. The graph 31 shows the progression of the algorithm and optimization of kinematic variables of a single muscle (flexor pollicis longus) and the added terms after each iteration. After the first iteration, the muscle length is approximated by (a, $M_1$, $M_2$, $M_4$, $M_5$, $M_{33}$) an intercept a was added in the step represented by block 15 for $P_L$, other terms came from the step represented by block 21 (from integration of moment arms polynomials). In the second iteration, the approximation expands using elements $M_{11}$, $M_{44}$, $M_{55}$, $M_{111}$, $M_{333}$, $M_{2222}$, and the precision of muscle length fit decreases below 1% (black line). In the fifth iteration, the moment arms around wrist extension-flexion, thumb MCP flexion and thumb DIP flexion have reached the minimum of AICc and were not improved any more. In the seventh iteration, the optimization of remaining kinematic parameters is finished.

The inventors identified how similar the muscles' structures obtained were with adherence to Eq. 2 (flow diagram of FIG. 4) and without adherence to Eq. 2 (flow diagram of FIG. 3). This difference was assessed using a similarity index (SI) that counted common elements in both structures. Structures of polynomials $L_A$ and $L_B$ corresponding to lengths of two muscles, muscles A and B, respectively, can be represented as: $L_A = P_C \cup P_{ANC}$, $L_B = P_C \cup P_{BNC}$, where $P_C$ is the shared structure of terms between $L_A$ and $L_B$; $P_{ANC}$ and $P_{BNC}$ are the non-common polynomial structures of terms present in A and not in B, and vice versa. Then, the similarity index is stated as: Equation 4

$$SI(A, B) = \frac{N_C}{N_{ANC} + N_{BNC} + N_C} \cdot 100\% \quad \text{Equation 4}$$

where $N_C$, $N_{ANC}$, $N_{BNC}$ are the number of terms in $P_C$, $P_{ANC}$, $P_{BNC}$, respectively. SI increases from 0% to 100% when the composition of identical terms increases in two polynomials. FIG. 7A shows that the use of Eq.2 in the search for polynomial terms (flow diagram 4) creates similar polynomials (mean SI>90). The use of Eq. 2 increases the search speed.

The inventors analyzed the similarity of polynomials from different muscles without the bias from the DOFs that each muscle crosses. To do that, the inventors introduced a DOF-independent polynomial vector for each muscle's musculotendon length polynomial. The Agnostic polynomial vector $v=(v_1, \ldots, v_n)^T$ of a polynomial is a nonnegative ($v_i \geq 0$) unit-vector ($\Sigma_i^n v_i^2 = 1$) with length equal to the number of possible term power compositions in a full polynomial of power ρ=5 and maximum muscle dimensionality d=6: n=18. Each element of the vector corresponds to a specific power combination in an ordered list. If a power combination on place i is present in a muscle length polynomial, then $v_i$ is equal to the modulus of the M coefficient (Eq. 1), otherwise $v_i = 0$. The order of power combinations is: [(1, 1, 1, 1, 1), (1, 1, 1, 1), (1, 1, 1, 2), (1, 1, 1), (1, 1, 2), (1, 1, 3), (1, 1), (1, 2, 2), (1, 2), (1, 3), (1, 4), (1), (2, 2), (2, 3), (2), (3), (4), (5)]. For example, letting $P_L = C_1 x_1 x_2^2 + C_2 x_1^2 x_2 + C_3 x_1^3 + C_4 x_1 + C_5 x_2 + C_6$, then its vector would have $[v_9 = |C_1| + |C_2|$; $v_{12} = |C_4| + |C_5|$; $v_{16} = |C_3|]$ and all other elements zero. The structural difference of two polynomials was obtained as the Euclidian distance between their vectors. The structural difference is minimal when power composition of all terms and their absolute coefficients are similar in both polynomials even if they cross different DOFs, and large when their power compositions do not have same terms.

The inventors calculated the amount of memory required for spline approximation as a size of MATLAB's '.mat' files that contained single-precision spline parameters saved using '-v7.3' flag, which enables compression. The inventors calculated the amount of memory required for polynomials as the size of executable '.mexw64' files compiled with Visual Studio 2017 C++ with '/O2' optimization. The amount of time required to perform the evaluation was obtained using MATLAB's Profiler. Individual samples for mean and standard deviation of evaluation time were obtained per muscle's dataset during estimation of quality of fit. All computations were performed on a regular personal computer (DELL Precision Workstation T5810 XL with Intel Xeon processor E5-2620 v3 2.4 GHz, 64 GB DDR4 RAM, SK Hynix SH920 512 GB SSD operating under Windows 10).

The composition of approximating polynomials was analyzed with standard statistical tools to test their validity. The root mean square values were used to evaluate errors in the approximated values relative to the dataset used for fitting and the independent testing dataset. The linear regression was used to test the relationship between the complexity of a muscle's physiological function in the form of the number of DOFs it spans and the complexity of the approximating polynomials.

The similarity of composition across multiple muscle groups was tested with the dimensionality reduction analyses, i.e., principle component analysis (PCA) and hierarchical clustering. The Euclidian distance between the muscle vectors in the DOF-independent basis (described above) was first analyzed with the average linkage hierarchical clustering implemented in SciPy. It is a common approach where the distance from a cluster to another cluster is an average distance between elements of these two clusters. Then, the dominant relationship in this distribution of muscle vectors was analyzed with PCA (Scikit-learn module).

The representation of structural and functional information within the polynomial structure was further tested by comparing the distributions of the distances between muscles with similar and different structure or function. The normality of these distributions was tested with D'Agostino's K-squared test that measures deviation from normal skewness and kurtosis. For normal distributions, a one-tailed t-test was used to test if distances between similar (functionally or structurally) muscles was smaller than distances between dissimilar muscles. The non-normal distributions were compared with Mann-Whitney U test (from SciPy module), which calculates the likelihood that a sample from one distribution will be less than a sample from another distribution. This test is nearly as efficient as t-test on normal distributions. Additionally, a simpler one-sample test was performed to compare the differences between elements in the two distributions to zero. A sign test was used to test if the median of that distribution was below zero. The sign test was used instead of the Wilcoxon signed-rank test, because the latter assumes symmetrical distribution of differences around the median.

Results

Approximation of Muscle Lengths and Moment Arms

Figures 6A, 6B:
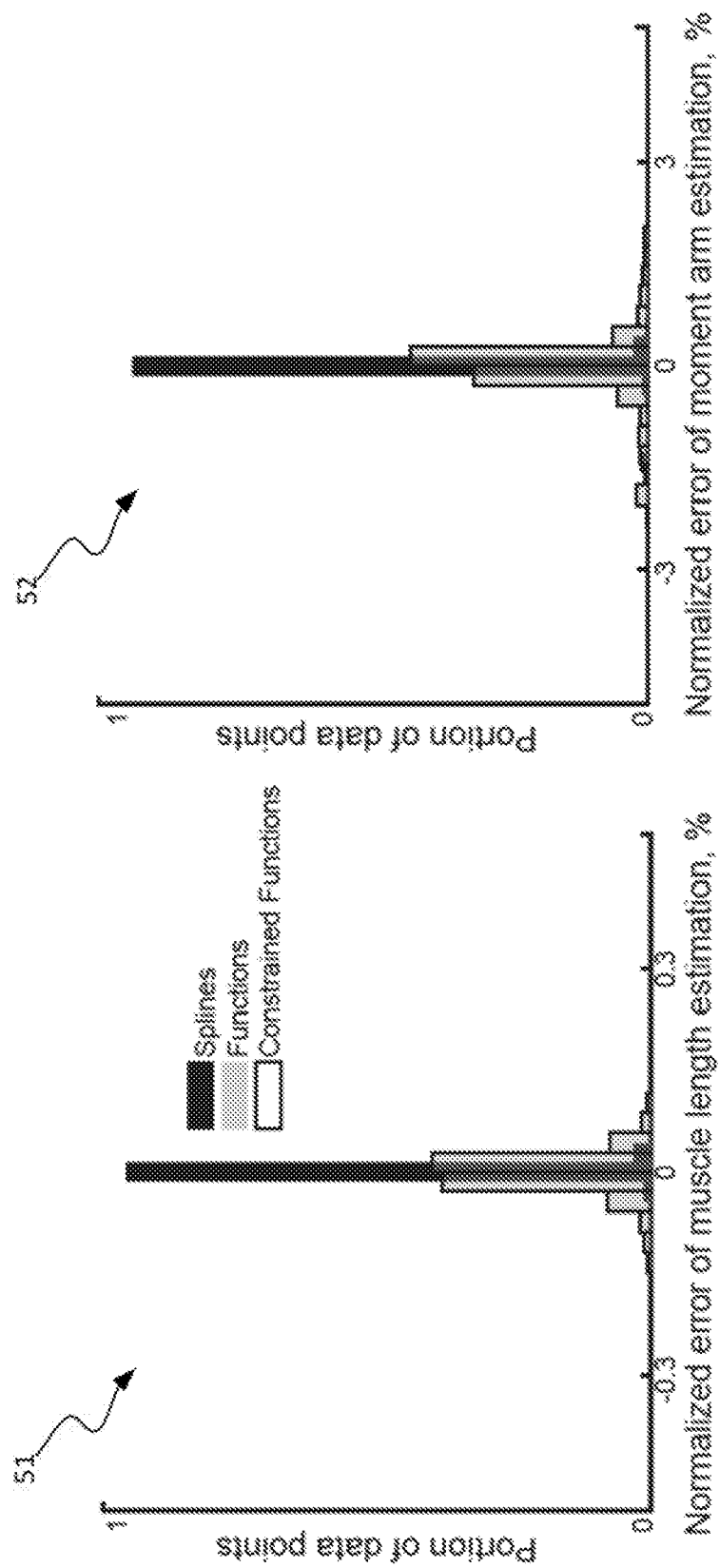
FIGS. 6A and 6B illustrate histograms of the normalized error in estimation of muscle lengths and moment arms, respectively, using splines and optimized polynomials with and without the aforementioned constraint associated with steps 11-13 of FIG. 4.

FIGS. 6A and 6B illustrate histograms 51 and 52 of the normalized error in estimation of muscle lengths and moment arms, respectively, using splines and optimized polynomials with and without the aforementioned constraint associated with steps 21-23 of FIG. 4. For the purposes of error visualization, 1% of outliers (see Table 1) are omitted. In this study, musculoskeletal kinematics of a human hand were precisely (error<3%, see Table 3 below) and efficiently (see Table 4 below) represented as a system of polynomials. FIG. 7A illustrates a graph 55 of similarity index (SI) vs. number of muscles for polynomials defined with the constraint stated as the equality between muscle length partial differentials in local coordinates and its moment arms. It demonstrates that methods described in FIG. 3 and FIG. 4 produce the muscle length polynomials of similar structure. FIG. 7B illustrates a graph 56 of the number of joints the muscle spans vs. the number of terms in the approximating polynomials, which demonstrates that the number of terms increases with the number of joints the muscle spans. FIG. 7B shows the relationship between the number of terms in the muscle length polynomial (circles) and the number of DOFs each muscle spans (dashed, $y=7.3112x-1.5604$, $r=0.7137$, $p<3\cdot10^{-6}$). The right side of FIG. 7B shows the distribution of polynomial complexity expressed as the number of terms.

Figure 8B:
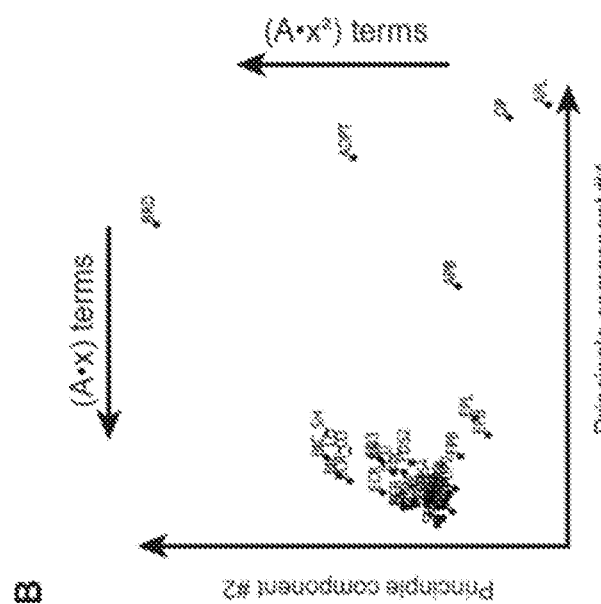
FIG. 8B shows all muscle vectors in the axes of the two first principle components: x-axis represents linear (x) terms and y-axis represents quadratic ($x^2$) terms.
Figure 8A:
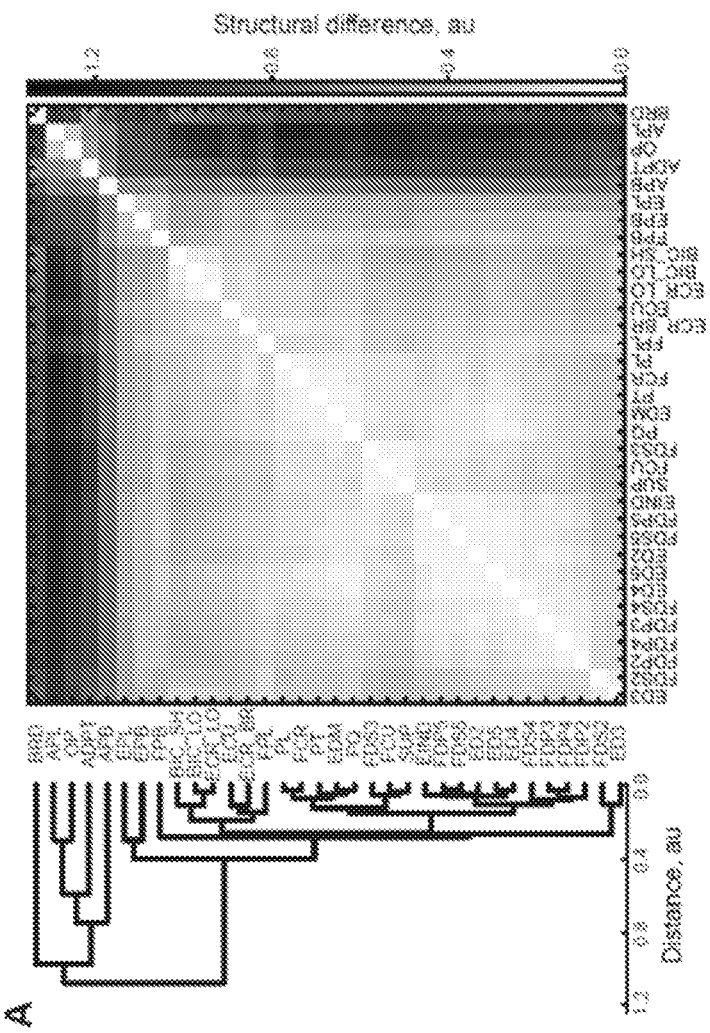
FIG. 8A shows an average-linkage dendrogram and the heatmap of distances between muscle vectors in the space defined by the polynomial terms that are independent of DOF identity.

FIGS. 8A and 8B demonstrate the non-random structure in the composition of polynomials. FIG. 8A shows an average-linkage dendrogram and heatmap of distances between DOF-independent vectors of muscles' lengths. FIG. 8B shows the muscle vectors in the axes of two first principal components corresponding to terms x (horizontal axis) and $x^2$ (vertical axis).

A combination of fitting and testing of the dataset was used to evaluate the precision of the known spline model and the polynomial model in accordance with the inventive principles and concepts. Splines and both types of polynomials (adhering and not adhering to the constraint described by Eq. 2) approximate moment arms with <3% error and muscle length with <0.2% error, as can be seen from FIGS. 6A and 6B and Table 3. Although the spline approximation error has a smaller deviation from zero, it is much harder to interpret (see Total number of parameters in Table 3). The AIC was used to assess the relative quality of statistical models to represent the phenomena by calculating the tradeoff between increasing precision and adding more variables. The AIC of the polynomial model of the kinematic variables ($-1.6*10^7$ and $-10^7$) is significantly smaller than AIC of the spline model ($2.2*10^9$ and $3.2*10^{10}$), which shows better relative quality of the polynomial model. Addition of the partial differential constraint (Eq. 2) did not significantly change the precision of the polynomial model ($p>0.95$ and Table 3) and AIC. Their error distributions in FIGS. 6A and 6B are not distinguishable.

TABLE 3

The comparison of spline and two polynomial approximations with (constrained) and without (unconstrained) the constraint linking muscle lengths and moment arms, as described by algorithm in Model Physical Constraints in Methods.

| Method | Normalized error, % | | Normalized error w/o outliers, % | | Total number of parameters | | AIC, au | |
|---|---|---|---|---|---|---|---|---|
| | L | MA | L | MA | L | MA | L | MA |
| CS | $-1*10^{-4} \pm 1.2*10^{-2}$, 1.23 | $-0.018 \pm 0.27$, 19.46 | $-1*10^{-4} \pm 5.8*10^{-3}$, 0.06 | $-0.018 \pm 0.22$, 1.85 | $1.1*10^9$ | $16.4*10^9$ | $2.2*10^9$ | $3.2*10^{10}$ |
| UP | $-2*10^{-4} \pm 5.2*10^{-2}$, 2.5 | $-0.024 \pm 0.65$, 18.68 | $-1*10^{-4} \pm 3.0*10^{-2}$, 0.14 | $-0.025 \pm 0.54$, 2.52 | 644 | 749 | $-1.6*10^7$ | $-1.0*10^7$ |
| CP | $-2*10^{-4} \pm 5.2*10^{-2}$, 17.77 | $-0.024 \pm 0.65$, | $-1*10^{-4} \pm 3.0*10^{-2}$, 0.14 | $-0.025 \pm 0.54$, 2.52 | 700 | 841 | $-1.6*10^7$ | $-1.0*10^7$ |

TABLE 3-continued

The comparison of spline and two polynomial approximations with (constrained) and without (unconstrained) the constraint linking muscle lengths and moment arms, as described by algorithm in Model Physical Constraints in Methods.

| Method | Normalized error, % | | Normalized error w/o outliers, % | | Total number of parameters | | AIC, au | |
|---|---|---|---|---|---|---|---|---|
| | L | MA | L | MA | L | MA | L | MA |
| | 2.4 | | | | | | | |

Values are given ±standard deviation and a maximum absolute percent. Approximation methods used: CS—cubic splines, UP—unconstrained polynomials, CP—constrained polynomials.

TABLE 4

Time and memory requirements of approximations methods for kinematic variables.

| Method | Time of evaluation, ms | Time of generation, min | Memory, KB |
|---|---|---|---|
| CS | 128.6633 ± 6.0872 | 33 | 17,800,000 |
| UP | 0.0147 ± 0.0017 | 297 | 139 |
| CP | 0.0161 ± 0.0030 | 114 | 166 |

The distribution of evaluation time for splines and polynomial models was obtained by separating the dataset into 30 muscle-based groups and measuring time spent evaluating the approximation function in each of the groups. Both polynomial models generated with and without Eq.2 (constrained and unconstrained) are evaluated faster than the spline approximation models (over $10^4$ times faster, Table 4) and require less memory ($10^5$ times smaller). When the relationship between muscle length and moment arm associated with Eq. 2 contributed to the selection of polynomial terms, as described above with reference to FIG. 4, the search time for the best-fit polynomial model decreased by a factor of at least two. This was accomplished without a change in the overall accuracy of fits, as demonstrated by FIGS. 6A and 6B.

Structure of Approximating Polynomials

Both polynomial models are similar in composition. We examined the difference in polynomial structure, i.e., the presence or absence of terms in functions for muscle lengths, calculated with and without adherence to the length-moment arm constraint (Eq. 2) for the same muscle. With reference again to FIG. 5, it shows that both optimizations found very close polynomials (SI≥30%) for a majority of muscles (29). On average, they have a 90% difference, and the maximum difference is about 35%. The differences in structures appear when the constrained polynomials retain the terms adopted from moment arm polynomials.

The number of polynomial terms in the muscle length grows with the number of degrees of freedom that a muscle crosses (FIG. 7B, r=0.71). However, the relative complexity of the polynomial measured in the fraction of parameter space occupied decreases. Interestingly, thumb muscles (ADPT, FPB, APB, EPB, APL, FPL, EPL) stay above the regression line, indicating a higher than average complexity, while finger muscles (FDS2-5, FDP2-5, ED2-5, EDM, EIND) stay below, suggesting a lower relative complexity.

Structure and Function

To investigate the information embedded within the polynomials of all muscles, the inventors developed DOF-independent vectors that represented the relative contribution of terms with specific power composition to the overall profile of muscle length polynomial. These nonnegative unit-vectors belong to a space where each axis corresponds to a power composition of a polynomial term with maximum total power of 5 (e.g. $x_i^2 x_j$ has power composition (2, 1)). Differences between muscles were then measured as Euclidean distances between their vectors. To visualize the resulting 18-dimensional space, the inventors generated a heatmap with a dendrogram (FIG. 8A) and projected these vectors on two first principle components (FIG. 8B).

It can be noted in FIGS. 8A and 8B that thumb muscles (ADPT, APB, OP, APL, and EPL, EPB, and FPB to lesser extent) are visibly separated from all other muscles. At the small relative distances, three clusters on the dendrogram and heatmap are visible. They can be assigned a function based on the majority of muscles within them: finger muscles (FDP2-5, FDS4, FDS5, ED2, ED4, ED5, EIND), wrist flexors and rotators located on the forearm (FCU, FCR, PT, PQ, SUP), biceps brachii and extensors (BIC_SH, BIC_LO, ECR_LO, ECR_BR, ECU). A large portion of the muscle vector variance (88%) is explained by the first two principle components. They have their largest coefficients associated with linear ($k_{12}$=−0.72) and square ($k_{15}$=0.83) power compositions, respectively (index 12 corresponds to axis associated with power combination (1) in the DOF-independent power vector, and 15-(2), see Methods). From that, the group of muscles in the bottom-left corner of FIG. 6B is dominated by linear terms, thumb muscles (bottom and bottom-right) rely on linear terms less than others, and brachioradialis (BRD) uses square term much more than the linear ($v_{12}$=0.18, $v_{15}$=0.95). Overall, the space of the muscle polynomial vectors appears to be not random and suggests internal organization based on muscle anatomy or function.

FIG. 9A is a graph 61 showing distributions 71 and 72 of distances between muscles that share an anatomical DOF (71) and between muscles that do not share a DOF (72). FIG. 9B is a graph 62 showing a probability density distribution 73 of difference in distance between muscles that share a DOF and muscles that do not. FIG. 9C is a graph 63 showing distributions 74 and 75 of distances between muscles that belong to the same functional group and share a DOF (74) and muscles that do not (75) but share a DOF. FIG. 9D is a graph 64 showing a probability density distribution 76 of difference in distance between muscles that belong to the same functional cluster and muscles that do not, while all of them share a DOF. Box plots in FIGS. 9A, 9B, 9C and 9D indicate a median and 25th-75th quantile region. Asterisks in FIG. 9ABCD indicate $p<10^{-8}$ in the statistical comparisons with $\alpha$=0.05.

To determine whether the muscle vectors contain information about their anatomical structure, the inventors performed a test to determine whether muscles crossing the same DOFs will be closer to each other in the vector space than to muscles that do not cross the DOF. To do that, the inventors generated three distributions: distances between muscles that share a DOF (FIG. 9A, bars 71); distances between muscles that do not share a DOF (FIG. 9A, bars 72); difference in distance (FIG. 9B, 73). The first distribution (bars 71) contains distances between two muscles, both crossing the DOF, for all DOFs. The second distribution (bars 72) contains distances between two muscles, one of which crosses the DOF, and the other one does not, for all DOFs. In this approach, the distance between two muscles may appear in the first distribution 71 when looking at one DOF, and the second 72, when looking at another DOF. The third distribution (FIG. 9B, 73) contains all possible differences in distance between muscles: DD=d(A,B)−d(A,C), where muscles A and B share a DOF, A and C do not, with respect to each DOF. Because of similarity between finger joints (MCP, PIP, DIP) of different fingers in our model and lack of hand-based finger muscles, MCP of fingers 2-5 were treated as equal in this analysis, as were PIP and DIP.

All three distributions 71-73 were not normal (D'Agostino, $p<10^{-8}$). The first two distributions 71 and 72 were significantly different with muscles that have similar anatomical paths being closer to each other (Mann-Whitney $U=8 \cdot 10^5$, $p<10^{-8}$). The median of the third distribution 73 was less than zero (sign test, $p<10^{-8}$). These results support that DOF-independent muscle vectors contain information on muscle anatomy. FIGS. 9A and 9B demonstrate that the polynomial term composition of the muscle length polynomials captures the anatomical relationship among muscles. FIGS. 9C and 9D demonstrate that the polynomial term composition of the muscle length polynomials captures the functional relationship among muscles.

To determine whether the muscle vectors contain information about their physiological function, not explained by the anatomical similarities, the inventors performed tests to determine whether muscles that share a DOF, but have different functions, will be farther apart than muscles that share a DOF and have similar function. Again, three distributions 74-76 were generated: distances between muscles that share a DOF and are within the same functional group (FIG. 9C, 74); distances between the muscles that share a DOF but belong to different functional groups (FIG. 9C, 75); difference in distance (FIG. 9D, 76). All modelled muscles were separated into seven functional groups: wrist supinators (BIC_LO, BIC_SH, BRD, SUP), pronators (PT, PQ), extensors (ECR_LO, ECR_BR, ECU), flexors (FCR, FCU, PL), finger flexors (FDS2-5, FDP2-5), extensors (ED2-5, EDM, EIND), and thumb muscles (APL, OP, APB, EPL, EPB, FPB, FPL, ADPT). Each muscle was assigned to a group based on its primary function in the hand and forearm.

All three distributions 74-76 were again not normal (D'Agostino, $p<10^{-8}$). The distributions 74 and 75 were significantly different with muscles that have similar function being closer to each other (Mann-Whitney $U=5 \cdot 10^6$, $p<10^{-8}$). The median of the third distribution 76 was less than zero (sign test, $p<10^{-8}$). These results support the conclusion that DOF-independent muscle vectors contain information on muscle function not explained by the muscle anatomy.

Although both tests showed significance, the median in FIG. 9B is almost twice as far from zero as the median in FIG. 9D (−0.13 and −0.07, respectively). In summary, these results support the idea that the polynomial term composition of muscle lengths is not random and reflects muscle anatomy and function.

Figure 10:
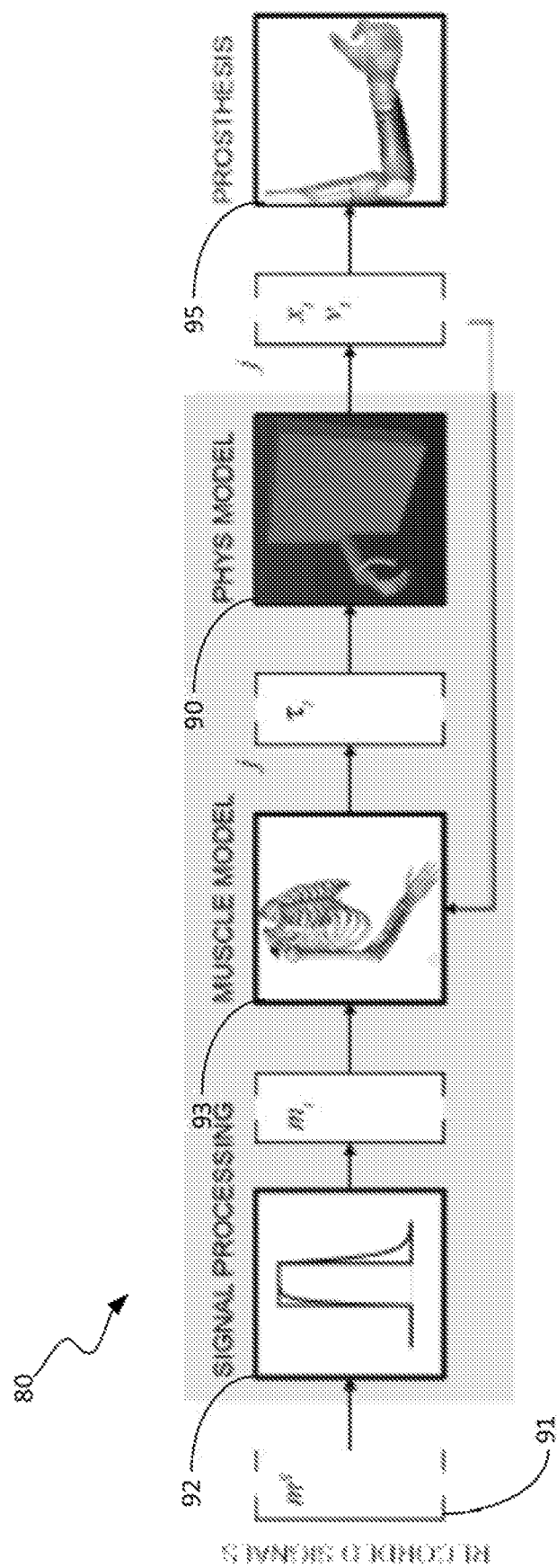
FIG. 10 is a diagram showing a system and method that enable biomimetic processing of biological inputs in order to predict desired prosthesis state from signals recorded in an amputee.
Figure 11:
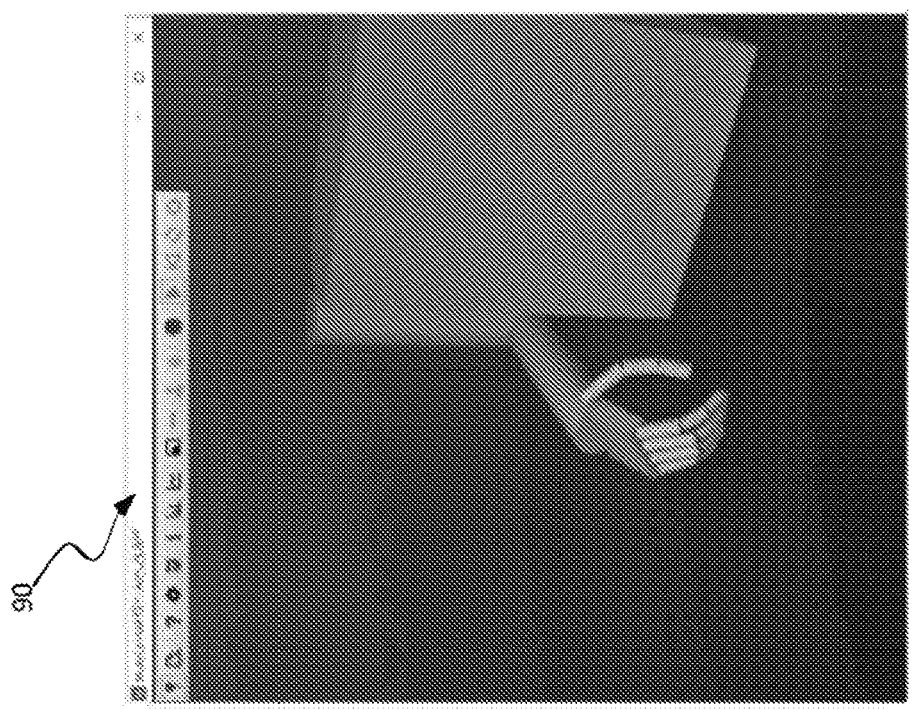
FIG. 11 shows a live physics model of a human hand in a simulated physics environment as examples.

FIG. 10 is a diagram showing a system 80 and demonstrating a method that enable biomimetic processing of biological inputs in order to predict desired prosthesis state from signals recorded in an amputee. FIG. 11 shows a live physics model 90 of a human hand in a simulated physics environment of MuJoCo or MuJoCo HAPTIX, as examples. MATLAB or other physics engines in software or hardware could also be used for the simulation. Recorded electromyography (EMG) signals 91 are input as the aforementioned input dataset. Signal processing circuitry 92 comprising one or more suitably configured processors or computers receives signal information from one or more sensors (not shown) and determines an amount of muscle that is activated. This amount parameter is input to a muscle model 93, which comprises the current structures of the polynomials at block 17 of the flow diagrams produced using the approximation method described above with reference to FIG. 3 or 4. As shown with a feedback loop, the muscle model 93 receives a joint position of the live physics model 90, produces a muscle length and one or more muscle moment arms for this point position, and forwards a torque to the physics model 90. The physics model 90 outputs a joint position and velocity to the prosthetic 95 in order to drive its motors (not shown).

Figure 12A:
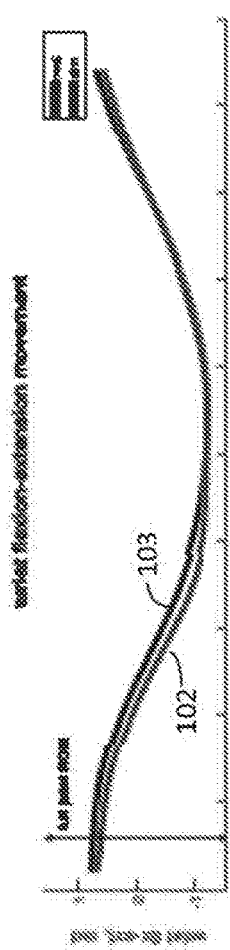
FIGS. 12A and 12B are graphs showing examples of real time performance of hand movements using the model of FIG. 11.
Figure 12B:
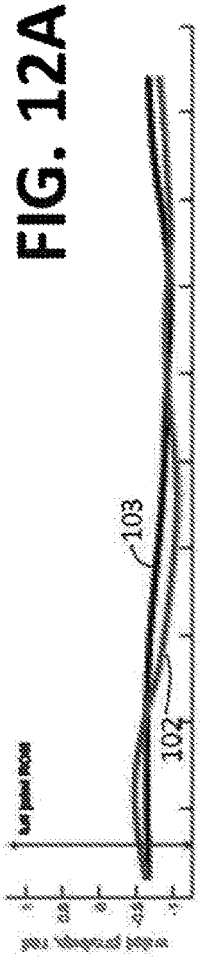
Figure 12C:
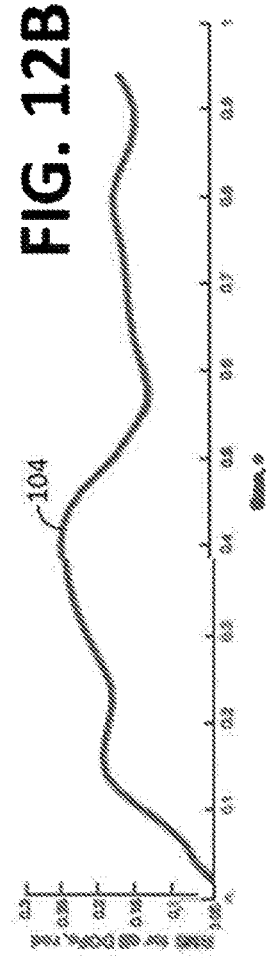
FIG. 12C is a graph that shows the root mean squared (RMS) average error for all DOF (including the fingers) using the model shown in FIG. 11.

FIGS. 12A and 12B are graphs of examples of real time performance of hand movements using the physics model 90 shown in FIGS. 10 and 11. These graphs show accuracy of reconstruction using the approximation method of the present disclosure. Surface electromyography (EMG) was recorded of a human flexing and extending a hand. The EMG signals were fed into the system 80 shown in FIG. 10 to produce a movement in the physics model 90. Reference numeral 102 represents the movement in the physics model 90 and reference numeral 103 represents the actual movement of the prosthetic 95, which is very close to the model movement. It can be seen from FIGS. 12A and 12B that the error between the modeled movement and the desired movement is low and there is no noticeable delay between them, because of the low computational cost of the created approximating polynomials. FIG. 12C shows the root mean squared (RMS) average 104 for all DOF (including the fingers). It can be seen from FIG. 12C that the errors between the signals for all DOFs is fairly low, which is due to the high precision of the approximation.

The approximation method described above is typically implemented in software, firmware, or a combination thereof, executed on one or more processors or computers. Alternatively, the approximation method may be implemented solely in hardware, such as a state machine or an application specific integrated circuit (ASIC), for example. The software, firmware, or combination thereof, is stored in one or more memory devices that may be part of the signal processing circuitry 92. When used for controlling a prosthetic 90, the signal processing circuitry 92 and any associated memory device may be mounted on, secured to or otherwise part of the prosthetic 90.

The approximation method can be used in applications that enable biomimetic control of external or implanted devices with complex dynamics. The musculoskeletal simulations enable the use of biological signals from the central nervous system that are expressed in a body-specific reference frame to generate actions that are appropriate for the control of arbitrary kinematic and dynamic actions required in human-machine tasks.

Inventive Aspects

In accordance with a first inventive aspect, an approximation method performed in a processor for generating a model is provided, wherein the approximation method comprises:

receiving an input dataset associated with at least a first muscle length and at least a first moment arm associated with the first muscle length;

using the input dataset to generate at least a first muscle length polynomial and at least a first moment arm polynomial associated with the first muscle length and said at least a first moment arm, respectively;

expanding the first muscle length polynomial by at least one additional term while improving an accuracy of the first muscle length polynomial based on information related to said at least a first moment arm;

expanding said at least a first moment arm polynomial by at least one additional term while improving an accuracy of said at least a first moment arm polynomial based on information related to the first muscle length; and approximating dynamics of the device based on the expanded first muscle length polynomial and the expanded first moment arm polynomial.

In accordance with a second inventive aspect, an approximation method performed in a processor for generating a model that controls a device is provided, wherein the approximation method comprises:

(1) receiving an input dataset associated with at least a first muscle length and at least a first moment arm associated with the first muscle length;

(2) using the input dataset to generate at least a first muscle length polynomial and at least a first moment arm polynomial associated with the first muscle length and said at least a first moment arm, respectively;

(3) expanding said first muscle length polynomial by at least one additional term and said at least a first moment arm polynomial by at least one additional term;

(4) determining whether or not the expanded polynomials are further expandable and whether or not further expansion will be beneficial to fitting the polynomials to the input dataset; and (5) if a determination is made that the expanded polynomials are not further expandable or that further expansion will not be beneficial to fitting the polynomials to the input data set, approximating dynamics of the device based on the expanded first muscle length polynomial and the expanded first moment arm polynomial.

In accordance with a third inventive aspect, the approximation method in accordance with the second inventive aspect further comprises:

if a determination is made at step (4) that the expanded polynomials are further expandable and that further expansion will be beneficial to fitting the polynomials to the input dataset, returning to step (3) and reiterating steps (3) through (5).

In accordance with a fourth inventive aspect, in the approximation method in accordance with the second inventive aspect, step (3) comprises:

generating at least a first list of potential candidates for expanding the first muscle length polynomial by at least one additional term and generating a second list for expanding the first moment arm polynomial by at least one additional term;

selecting a first candidate from the first list for expanding the first muscle length polynomial and selecting a second candidate from the second list for expanding the first moment arm polynomial; and expanding the first muscle length polynomial by the first candidate and expanding the first moment arm polynomial by the second candidate.

In accordance with a fifth inventive aspect, the approximation method in accordance with the fourth inventive aspect further comprises:

during step (3), after expanding the first muscle length polynomial by the first candidate and expanding the first moment arm polynomial by the second candidate:

integrating the expanded first moment arm polynomial to produce one or more integrals;

joining said one or more integrals with the expanded first muscle length polynomial to obtain a constrained muscle length polynomial; and differentiating the constrained muscle length polynomial to obtain one or more constrained moment arm polynomials, and wherein step (4) makes the determination of whether or not the expanded polynomials are further expandable and whether or not further expansion will be beneficial to fitting the polynomials to the input data set based on the constrained muscle length polynomial and said one or more constrained moment arm polynomials.

In accordance with a sixth inventive aspect, in the approximation method according to the fourth inventive aspect, during step (3), selecting the first candidate from the first list comprises:

analyzing all of the potential candidates on the first list to determine which of the potential candidates on the first list results in a greatest improvement in fitting the expanded muscle length polynomial to the input dataset.

In accordance with a seventh inventive aspect, in the approximation method according to the fourth inventive aspect, during step (3), selecting the first candidate from the first list comprises:

analyzing all of the potential candidates on the second list to determine which of the potential candidates on the second list results in a greatest improvement in fitting the expanded first moment arm polynomial to the input dataset.

In accordance with an eighth inventive aspect, in the approximation method according to the seventh inventive aspect, an Akaike information criterion (AIC) is calculated for the input dataset and used in the analysis that determines which of the potential candidates on the first and second lists result in the greatest improvement in fitting the expanded muscle length polynomial and the expanded first moment arm polynomial, respectively, to the input dataset.

In accordance with an ninth inventive aspect, the approximation method comprises:

(1) receiving an input dataset associated with at least a first muscle length and at least a first moment arm associated with the first muscle length;

(2) using the input dataset to generate at least a first muscle length polynomial and at least a first moment arm polynomial associated with the first muscle length and said at least a first moment arm, respectively;

(3) expanding said first muscle length polynomial by at least one additional term and said at least a first moment arm polynomial by at least one additional term;

(4) integrating said at least a first moment arm polynomial to produce one or more integrals;

(5) joining said one or more integrals with the first muscle length polynomial to obtain a constrained muscle length polynomial;

(6) differentiating the constrained muscle length polynomial to obtain one or more constrained moment arm polynomials;

(7) determining whether or not the constrained muscle length polynomial and said one or more constrained moment arm polynomials are further expandable and whether or not further expansion will be beneficial to fitting the constrained muscle length and moment arm polynomials to the input dataset; and (8) if a determination is made that the further expansion is not possible or that further expansion will not be beneficial, approximating dynamics of the device based on the constrained muscle length and moment arm polynomials obtained at step (6).

In accordance with a tenth inventive aspect, the approximation method according to the ninth inventive aspect further comprises:

if a determination is made at step (7) that the constrained muscle length and moment arm polynomials are further expandable and that further expansion will be beneficial, returning to step (3) and reiterating steps (3) through (8).

In accordance with an eleventh inventive aspect, in the approximation method according to the ninth inventive aspect, step (3) comprises:

generating at least a first list of potential candidates for expanding the first muscle length polynomial by at least one additional term and generating a second list for expanding the first moment arm polynomial by at least one additional term;

selecting a first candidate from the first list for expanding the first muscle length polynomial and selecting a second candidate from the second list for expanding the first moment arm polynomial; and expanding the first muscle length polynomial by the first candidate and expanding the first moment arm polynomial by the second candidate.

In accordance with a twelfth inventive aspect, in the approximation method according to the eleventh inventive aspect, during step (3), selecting the first candidate from the first list for expanding the first muscle length polynomial by at least one additional term comprises:

analyzing all of the potential candidates on the first list to determine which of the potential candidates on the first list results in a greatest improvement in fitting the first muscle length polynomial to the input dataset.

In accordance with a thirteenth inventive aspect, in the approximation method according to the eleventh inventive aspect, during step (3), selecting the second candidate from the second list for expanding said at least a first moment arm polynomial by at least one additional term comprises:

analyzing all of the potential candidates on the second list to determine which of the potential candidates on the second list results in a greatest improvement in fitting the expanded first moment arm polynomial to the input dataset.

In accordance with a fourteenth inventive aspect, in the approximation method according to the thirteenth inventive aspect, an AIC is calculated for the input dataset and used in the analysis that determines which of the potential candidates on the first and second lists result in the greatest improvement in fitting the expanded muscle length polynomial and the expanded first moment arm polynomial, respectively, to the input dataset.

In accordance with a fifteenth inventive aspect, a system for generating a model is provided comprising:

one or more processors comprising:

first logic configured to perform a first process that receives an input dataset associated with at least a first muscle length and at least a first moment arm associated with the first muscle length;

second logic configured to perform a second process that uses the input dataset to generate at least a first muscle length polynomial and at least a first moment arm polynomial associated with the first muscle length and said at least a first moment arm, respectively;

third logic configured to perform a third process that expands said first muscle length polynomial by at least one additional term and said at least a first moment arm polynomial by at least one additional term;

fourth logic configured to perform a fourth process that determines whether or not the expanded polynomials are further expandable and whether or not further expansion will be beneficial to fitting the polynomials to the input dataset; and fifth logic configured to perform a fifth process that approximates dynamics of the device based on the expanded first muscle length polynomial and the expanded first moment arm polynomial if a determination is made by the fourth process performed by the fourth logic that the expanded polynomials are not further expandable or that further expansion will not be beneficial to fitting the polynomials to the input data set In accordance with a sixteenth inventive aspect, in the system according to the fifteenth inventive aspect, if a determination is made by the fourth logic performing the fourth process that the expanded polynomials are further expandable and that further expansion will be beneficial to fitting the polynomials to the input dataset, the system returns to the third process and the third through fifth logic perform the third through fifth processes, respectively.

In accordance with a seventeenth inventive aspect, in the system according to the fifteenth inventive aspect, the third process performed by the third logic comprises:

generating at least a first list of potential candidates for expanding the first muscle length polynomial by at least one additional term and generating a second list for expanding the first moment arm polynomial by at least one additional term;

selecting a first candidate from the first list for expanding the first muscle length polynomial and selecting a second candidate from the second list for expanding the first moment arm polynomial; and expanding the first muscle length polynomial by the first candidate and expanding the first moment arm polynomial by the second candidate.

In accordance with an eighteenth inventive aspect, in the system according to the seventeenth inventive aspect, the third process performed by the third logic further comprises:

integrating the expanded first moment arm polynomial to produce one or more integrals after the third process expands the first muscle length polynomial by the first candidate and expands the first moment arm polynomial by the second candidate;

joining said one or more integrals with the expanded first muscle length polynomial to obtain a constrained muscle length polynomial; and differentiating the constrained muscle length polynomial to obtain one or more constrained moment arm polynomials, and wherein step (4) makes the determination of whether or not the expanded polynomials are further expandable and whether or not further expansion will be beneficial to fitting the polynomials to the input data set based on the constrained muscle length polynomial and said one or more constrained moment arm polynomials.

In accordance with a nineteenth inventive aspect, in the system according to the seventeenth inventive aspect, during the third process, selecting the first candidate from the first list comprises:
analyzing all of the potential candidates on the first list to determine which of the potential candidates on the first list results in a greatest improvement in fitting the expanded muscle length polynomial to the input dataset.

In accordance with a twentieth inventive aspect, in the system according to the seventeenth inventive aspect, during the third process, selecting the second candidate from the second list comprises:
analyzing all of the potential candidates on the second list to determine which of the potential candidates on the second list results in a greatest improvement in fitting the expanded first moment arm polynomial to the input dataset.

In accordance with a twenty-first inventive aspect, in the system according to the twentieth inventive aspect, an AIC is calculated for the input dataset and used in the analysis that determines which of the potential candidates on the first and second lists result in the greatest improvement in fitting the expanded muscle length polynomial and the expanded first moment arm polynomial, respectively, to the input dataset.

In accordance with a twenty-second inventive aspect, a system for generating a model is provided comprising:
one or more processors comprising:
first logic configured to perform a first process that receives an input dataset associated with at least a first muscle length and at least a first moment arm associated with the first muscle length;
second logic configured to perform a second process that uses the input dataset to generate at least a first muscle length polynomial and at least a first moment arm polynomial associated with the first muscle length and said at least a first moment arm, respectively;
third logic configured to perform a third process that expands said first muscle length polynomial by at least one additional term and said at least a first moment arm polynomial by at least one additional term;
fourth logic configured to perform a fourth process that integrates said at least a first moment arm polynomial to produce one or more integrals;
fifth logic configured to perform a fifth process that joins said one or more integrals with the first muscle length polynomial to obtain a constrained muscle length polynomial;
sixth logic configured to perform a sixth process that differentiates the constrained muscle length polynomial to obtain one or more constrained moment arm polynomials;
seventh logic configured to perform a seventh process that determines whether or not the constrained muscle length polynomial and said one or more constrained moment arm polynomials are further expandable and whether or not further expansion will be beneficial to fitting the constrained muscle length and moment arm polynomials to the input dataset; and
eighth logic configured to perform an eighth process that approximates dynamics of the device based on the constrained muscle length and moment arm polynomials obtained by the sixth logic if a determination is made that the further expansion is not possible or that further expansion will not be beneficial.

In accordance with a twenty-third inventive aspect, in the system according to the twenty-second aspect, if a determination is made by the seventh process that the constrained muscle length and moment arm polynomials are further expandable and that further expansion will be beneficial, the system returns to the third process and causes the third through eighth logic to reiterate the third through eighth processes, respectively.

In accordance with a twenty-fourth inventive aspect, in the system according to the twenty-third aspect, the third process comprises:
generating at least a first list of potential candidates for expanding the first muscle length polynomial by at least one additional term and generating a second list for expanding the first moment arm polynomial by at least one additional term;
selecting a first candidate from the first list for expanding the first muscle length polynomial and selecting a second candidate from the second list for expanding the first moment arm polynomial; and
expanding the first muscle length polynomial by the first candidate and expanding the first moment arm polynomial by the second candidate.

In accordance with a twenty-fifth inventive aspect, in the system according to the twenty-fourth aspect, during the third process, selecting the first candidate from the first list for expanding the first muscle length polynomial by at least one additional term comprises:
analyzing all of the potential candidates on the first list to determine which of the potential candidates on the first list results in a greatest improvement in fitting the first muscle length polynomial to the input dataset.

In accordance with a twenty-sixth inventive aspect, in the system according to the twenty-fourth aspect, during the third process, during the third process, selecting the second candidate from the second list for expanding said at least a first moment arm polynomial by at least one additional term comprises:
analyzing all of the potential candidates on the second list to determine which of the potential candidates on the second list results in a greatest improvement in fitting the expanded first moment arm polynomial to the input dataset.

In accordance with a twenty-seventh inventive aspect, in the system according to the twenty-sixth aspect, an AIC is calculated for the input dataset and used in the analysis of the third process that determines which of the potential candidates on the first and second lists result in the greatest improvement in fitting the expanded muscle length polynomial and the expanded first moment arm polynomial, respectively, to the input dataset.

In accordance with a twenty-eighth inventive aspect, in the system according to the twenty-second inventive aspect, an AIC is calculated for the input dataset and used in the analysis of the third process that determines which of the potential candidates on the first and second lists result in the greatest improvement in fitting the expanded muscle length polynomial and the expanded first moment arm polynomial, respectively, to the input dataset.

In accordance with a twenty-ninth inventive aspect, a method is provided for more quickly controlling a prosthetic by reducing computational processing time in a muscle model that can be used to control the prosthetic, comprising:

computing a polynomial equation for a muscle that defines approximate values f(x) of muscle lengths, muscle moment arms, or both, in relation to a joint having a plurality of degrees of freedom (DOF) with the following equation:

$$f(x) = a + \sum_{i}^{\rho}\sum_{k}^{d} P_{ki}x_k^i + \sum_{i=2}^{\rho-1}\sum_{j}^{i-1}\sum_{k,l}^{d} M_{kil(i-j)}x_k^j x_l^{i-j}$$

wherein a is a constant; x is a multidimensional vector describing a state of each degree of freedom (DOF); ρ is a maximum power of the polynomial equation; d is a number of DOF; P is a non-interacting power matrix; and M is an interacting power tensor.

In accordance with a thirtieth inventive aspect, a method is provided for more quickly controlling a prosthetic by reducing computational processing time in a muscle model that can be used to control the prosthetic, comprising:

computing a polynomial equation for a muscle that defines approximate values f(x) of muscle lengths, muscle moment arms, or both, in relation to a joint having a plurality of degrees of freedom (DOF) by including or not including polynomial terms based upon an error between polynomial produced data and recorded data associated with each of the terms.

In accordance with a thirty-first inventive aspect, in the method according to the thirtieth inventive aspect, the inclusion or non-inclusion of each of the polynomial terms is based upon the information tradeoff criterion of the Shannon principal.

In accordance with a thirty-first inventive aspect, the method according to the thirty-first inventive aspect further comprises adding at least one polynomial term that represents a relationship between the joint and another joint.

In accordance with a thirty-second inventive aspect, a prosthetic is provided, comprising:

means for storing a first polynomial equation for a muscle that defines approximate values f(x) of muscle lengths in relation to a joint having a plurality of degrees of freedom (DOF) with the following equation:

$$f(x) = a + \sum_{i}^{\rho}\sum_{k}^{d} P_{ki}x_k^i + \sum_{i=2}^{\rho-1}\sum_{j}^{i-1}\sum_{k,l}^{d} M_{kil(i-j)}x_k^j x_l^{i-j}$$

wherein a is a constant; x is a multidimensional vector describing a state of each degree of freedom (DOF); ρ is a maximum power of the polynomial equation; d is a number of DOF; P is a non-interacting power matrix; and M is an interacting power tensor; and means for storing a second polynomial equation for a muscle that defines approximate values f(x) of muscle moment arms in relation to the joint having a plurality of degrees of freedom (DOF) with the following equation:

$$f(x) = a + \sum_{i}^{\rho}\sum_{k}^{d} P_{ki}x_k^i + \sum_{i=2}^{\rho-1}\sum_{j}^{i-1}\sum_{k,l}^{d} M_{kil(i-j)}x_k^j x_l^{i-j}$$

wherein a is a constant; x is a multidimensional vector describing a state of each degree of freedom (DOF); ρ is a maximum power of the polynomial equation; d is a number of DOF; P is a non-interacting power matrix; and M is an interacting power tensor.

In accordance with a thirty-third inventive aspect, a prosthetic is provided, comprising:
(a) a movable part;
(b) a memory storing computer software;
(c) a processor that can execute the software, the software comprising:
  (1) code that defines a first polynomial equation for a muscle that defines approximate values f(x) of muscle lengths in relation to a joint having a plurality of degrees of freedom (DOF) with the following equation:

$$f(x) = a + \sum_{i}^{\rho}\sum_{k}^{d} P_{ki}x_k^i + \sum_{i=2}^{\rho-1}\sum_{j}^{i-1}\sum_{k,l}^{d} M_{kil(i-j)}x_k^j x_l^{i-j}$$

wherein a is a constant; x is a multidimensional vector describing a state of each degree of freedom (DOF); ρ is a maximum power of the polynomial equation; d is a number of DOF; P is a non-interacting power matrix; and M is an interacting power tensor; and
  (2) code that defines a second polynomial equation for a muscle that defines approximate values f(x) of muscle moment arms in relation to the joint having a plurality of degrees of freedom (DOF) with the following equation:

$$f(x) = a + \sum_{i}^{\rho}\sum_{k}^{d} P_{ki}x_k^i + \sum_{i=2}^{\rho-1}\sum_{j}^{i-1}\sum_{k,l}^{d} M_{kil(i-j)}x_k^j x_l^{i-j}$$

wherein a is a constant; x is a multidimensional vector describing a state of each degree of freedom (DOF); ρ is a maximum power of the polynomial equation; d is a number of DOF; P is a non-interacting power matrix; and M is an interacting power tensor.

In accordance with a thirty-fourth inventive aspect, a method is provided for identification of muscle structure and physiological function based on a composition of one or more polynomials, comprising:

using an input dataset to generate at least a first muscle length polynomial associated with a first muscle, the first muscle length polynomial having a first set of coefficients;

obtaining a vector from the first set of coefficients, the vector having a set of elements, wherein each element of the vector corresponds to a specific power combination in an ordered list; and determining a description of a structure and function of the first muscle based on the vector.

In accordance with a thirty-fifth inventive aspect, the method according to the thirty-fourth inventive aspect further comprises identifying a graft location for an autotransplant of the first muscle based on the vector.

In accordance with a thirty-sixth inventive aspect, the method according to the thirty-fourth inventive aspect further comprises using the description of the structure of the muscle to generate desired muscle functionality to prevent actuation of a joint associated with the first muscle from resulting in a risk of injury to the joint or the first muscle.

It should be emphasized that the above-described embodiments of the present invention, particularly, any "preferred"

embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure.

For example, while the inventive principles and concepts have been described herein with reference to controlling a prosthetic 50, the described software and/or firmware can be used in other applications that require fast and memory-efficient approximation of complex multidimensional data, such as, for example, with robots or autonomous drones controlled by small chips that need to approximate information about interactions with objects or terrain, that are originally calculated using systems of differential equations.

The invention claimed is:

1. An approximation method performed in a processor for generating a model, the approximation method comprising:
    receiving an input dataset associated with at least a first muscle length and at least a first moment arm associated with the first muscle length;
    using the input dataset to generate at least a first muscle length polynomial and at least a first moment arm polynomial associated with the first muscle length and said at least a first moment arm, respectively;
    expanding the first muscle length polynomial by at least one additional term while improving an accuracy of the first muscle length polynomial based on information related to said at least a first moment arm;
    expanding said at least a first moment arm polynomial by at least one additional term while improving an accuracy of said at least a first moment arm polynomial based on information related to the first muscle length;
    integrating the expanded first moment polynomial to produce one or more integrals;
    joining said one or more integrals with the expanded first muscle length polynomial to obtain a constrained muscle length polynomial;
    differentiating the constrained muscle length polynomial to obtain one or more constrained moment arm polynomials; and
    approximating dynamics of a device based at least in part on the expanded first muscle length polynomial, the expanded first moment arm polynomial, the constrained muscle length polynomial, and the one or more constrained moment arm polynomials.

2. The approximation method of claim 1, wherein expanding the first muscle length polynomial and expanding the first moment arm polynomial further comprises:
    generating at least a first list of potential candidates for expanding the first muscle length polynomial by at least one additional term and generating a second list for expanding the first moment arm polynomial by at least one additional term;
    selecting a first candidate from the first list for expanding the first muscle length polynomial and selecting a second candidate from the second list for expanding the first moment arm polynomial; and
    expanding the first muscle length polynomial by the first candidate and expanding the first moment arm polynomial by the second candidate.

3. The approximation method of claim 2, wherein selecting the first candidate from the first list comprises:
    analyzing all of the potential candidates on the first list to determine which of the potential candidates on the first list results in a greatest improvement in fitting the expanded muscle length polynomial to the input dataset.

4. The approximation method of claim 3, wherein selecting the second candidate from the second list comprises:
    analyzing all of the potential candidates on the second list to determine which of the potential candidates on the second list results in a greatest improvement in fitting the expanded first moment arm polynomial to the input dataset.

5. An approximation method performed in a processor for generating a model, the approximation method comprising:
    (1) receiving an input dataset associated with at least a first muscle length and at least a first moment arm associated with the first muscle length;
    (2) using the input dataset to generate at least a first muscle length polynomial and at least a first moment arm polynomial associated with the first muscle length and said at least a first moment arm, respectively;
    (3) generating expanded polynomials comprising an expanded first muscle length polynomial and an expanded first moment arm polynomial by:
        generating at least a first list of potential candidates for expanding the first muscle length polynomial by at least one additional term and generating a second list for expanding the first moment arm polynomial by at least one additional term;
        selecting a first candidate from the first list for expanding the first muscle length polynomial and selecting a second candidate from the second list for expanding the first moment arm polynomial;
        expanding the first muscle length polynomial by the first candidate and expanding the first moment arm polynomial by the second candidate;
        integrating the expanded first moment arm polynomial to produce one or more integrals;
        joining said one or more integrals with the expanded first muscle length polynomial to obtain a constrained muscle length polynomial; and
        differentiating the constrained muscle length polynomial to obtain one or more constrained moment arm polynomials;
    (4) determining whether or not the expanded polynomials are further expandable and whether or not further expansion will be beneficial to fitting the expanded polynomials to the input dataset based on the constrained muscle length polynomial and said one or more constrained moment arm polynomials; and
    (5) if a determination is made that the expanded polynomials are not further expandable or that further expansion will not be beneficial to fitting the expanded polynomials to the input dataset, approximating dynamics of a device based on the expanded first muscle length polynomial and the expanded first moment arm polynomial.

6. The approximation method of claim 5, the method further comprising:
    if a determination is made at step (4) that the expanded polynomials are further expandable and that further expansion will be beneficial to fitting the expanded polynomials to the input dataset, returning to step (3) and reiterating steps (3) through (5).

7. An approximation method performed in a processor for generating a model, the approximation method comprising:
    (1) receiving an input dataset associated with at least a first muscle length and at least a first moment arm associated with the first muscle length;

(2) using the input dataset to generate at least a first muscle length polynomial and at least a first moment arm polynomial associated with the first muscle length and said at least a first moment arm, respectively;

(3) generating expanded polynomials comprising an expanded first muscle length polynomial and an expanded first moment arm polynomial by:

generating at least a first list of potential candidates for expanding the first muscle length polynomial by at least one additional term and generating a second list for expanding the first moment arm polynomial by at least one additional term, wherein an Akaike information criterion (AIC) is calculated for the input dataset;

selecting a first candidate from the first list for expanding the first muscle length polynomial and selecting a second candidate from the second list for expanding the first moment arm polynomial, wherein the AIC is used in analysis that determines which of the potential candidates on the first and second lists result in the greatest improvement in fitting the expanded muscle length polynomial and the expanded first moment arm polynomial, respectively, to the input dataset; and expanding the first muscle length polynomial by the first candidate and expanding the first moment arm polynomial by the second candidate;

(4) determining whether or not the expanded polynomials are further expandable and whether or not further expansion will be beneficial to fitting the expanded polynomials to the input dataset; and (5) if a determination is made that the expanded polynomials are not further expandable or that further expansion will not be beneficial to fitting the expanded polynomials to the input dataset, approximating dynamics of a device based on the expanded first muscle length polynomial and the expanded first moment arm polynomial.

8. An approximation method performed on a processor for generating a model, the approximation method comprising:

(1) receiving an input dataset associated with at least a first muscle length and at least a first moment arm associated with the first muscle length;

(2) using the input dataset to generate at least a first muscle length polynomial and at least a first moment arm polynomial associated with the first muscle length and said at least a first moment arm, respectively;

(3) expanding said first muscle length polynomial by at least one additional term and said at least a first moment arm polynomial by at least one additional term;

(4) integrating said at least a first moment arm polynomial to produce one or more integrals;

(5) joining said one or more integrals with the first muscle length polynomial to obtain a constrained muscle length polynomial;

(6) differentiating the constrained muscle length polynomial to obtain one or more constrained moment arm polynomials;

(7) determining whether or not the constrained muscle length polynomial and said one or more constrained moment arm polynomials are further expandable and whether or not further expansion will be beneficial to fitting the constrained muscle length and moment arm polynomials to the input dataset; and (8) if a determination is made that the further expansion is not possible or that further expansion will not be beneficial, approximating dynamics of a device based on the constrained muscle length and moment arm polynomials obtained at step (6).

9. The approximation method of claim 8, further comprising:

if a determination is made at step (7) that the constrained muscle length and moment arm polynomials are further expandable and that further expansion will be beneficial, returning to step (3) and reiterating steps (3) through (8).

10. The method of claim 8, wherein step (3) comprises:

generating at least a first list of potential candidates for expanding the first muscle length polynomial by at least one additional term and generating a second list for expanding the first moment arm polynomial by at least one additional term;

selecting a first candidate from the first list for expanding the first muscle length polynomial and selecting a second candidate from the second list for expanding the first moment arm polynomial; and expanding the first muscle length polynomial by the first candidate and expanding the first moment arm polynomial by the second candidate.

11. The method of claim 10, wherein during step (3), selecting the first candidate from the first list for expanding the first muscle length polynomial by at least one additional term comprises:

analyzing all of the potential candidates on the first list to determine which of the potential candidates on the first list results in a greatest improvement in fitting the first muscle length polynomial to the input dataset.

12. The method of claim 11, wherein during step (3), selecting the second candidate from the second list for expanding said at least a first moment arm polynomial by at least one additional term comprises:

analyzing all of the potential candidates on the second list to determine which of the potential candidates on the second list results in a greatest improvement in fitting the expanded first moment arm polynomial to the input dataset.

13. The method of claim 12, wherein an Akaike information criterion (AIC) is calculated for the input dataset and used in the analysis that determines which of the potential candidates on the first and second lists result in the greatest improvement in fitting the expanded muscle length polynomial and the expanded first moment arm polynomial, respectively, to the input dataset.

14. A system for generating a model, the system comprising:

one or more processors comprising:

first logic configured to perform a first process that receives an input dataset associated with at least a first muscle length and at least a first moment arm associated with the first muscle length;

second logic configured to perform a second process that uses the input dataset to generate at least a first muscle length polynomial and at least a first moment arm polynomial associated with the first muscle length and said at least a first moment arm, respectively;

third logic configured to perform a third process that generates expanded polynomials comprising an expanded first muscle length polynomial and an expanded first moment arm polynomial by:

generating at least a first list of potential candidates for expanding the first muscle length polynomial by at least one additional term and generating a second list for expanding the first moment arm polynomial by at least one additional term;

selecting a first candidate from the first list for expanding the first muscle length polynomial and selecting a second candidate from the second list for expanding the first moment arm polynomial;

expanding the first muscle length polynomial by the first candidate and expanding the first moment arm polynomial by the second candidate;

integrating the expanded first moment arm polynomial to produce one or more integrals after the third process expands the first muscle length polynomial by the first candidate and expands the first moment arm polynomial by the second candidate;

joining said one or more integrals with the expanded first muscle length polynomial to obtain a constrained muscle length polynomial; and differentiating the constrained muscle length polynomial to obtain one or more constrained moment arm polynomials;

fourth logic configured to perform a fourth process that determines whether or not the expanded polynomials are further expandable and whether or not further expansion will be beneficial to fitting the expanded polynomials to the input dataset based on the constrained muscle length polynomial and said one or more constrained moment arm polynomials; and fifth logic configured to perform a fifth process that approximates dynamics of a device based on the expanded first muscle length polynomial and the expanded first moment arm polynomial if a determination is made by the fourth process performed by the fourth logic that the expanded polynomials are not further expandable or that further expansion will not be beneficial to fitting the expanded polynomials to the input dataset.

15. The system of claim 14, wherein if a determination is made by the fourth logic performing the fourth process that the expanded polynomials are further expandable and that further expansion will be beneficial to fitting the expanded polynomials to the input dataset, the system returns to the third process and the third through fifth logic perform the third through fifth processes, respectively.

16. The system of claim 14, wherein during the third process, selecting the first candidate from the first list comprises:

analyzing all of the potential candidates on the first list to determine which of the potential candidates on the first list results in a greatest improvement in fitting the expanded muscle length polynomial to the input dataset.

17. The system of claim 16, wherein during the third process, selecting the second candidate from the second list comprises:

analyzing all of the potential candidates on the second list to determine which of the potential candidates on the second list results in a greatest improvement in fitting the expanded first moment arm polynomial to the input dataset.

18. The system of claim 17, wherein an Akaike information criterion (AIC) is calculated for the input dataset and used in the analysis that determines which of the potential candidates on the first and second lists result in the greatest improvement in fitting the expanded muscle length polynomial and the expanded first moment arm polynomial, respectively, to the input dataset.

19. A system for generating a model, the system comprising:

one or more processors comprising:

first logic configured to perform a first process that receives an input dataset associated with at least a first muscle length and at least a first moment arm associated with the first muscle length;

second logic configured to perform a second process that uses the input dataset to generate at least a first muscle length polynomial and at least a first moment arm polynomial associated with the first muscle length and said at least a first moment arm, respectively;

third logic configured to perform a third process that generates expanded polynomials comprising an expanded first muscle length polynomial and an expanded first moment arm polynomial by expanding said first muscle length polynomial by at least one additional term and said at least a first moment arm polynomial by at least one additional term;

fourth logic configured to perform a fourth process that integrates said at least a first moment arm polynomial to produce one or more integrals;

fifth logic configured to perform a fifth process that joins said one or more integrals with the first muscle length polynomial to obtain a constrained muscle length polynomial;

sixth logic configured to perform a sixth process that differentiates the constrained muscle length polynomial to obtain one or more constrained moment arm polynomials;

seventh logic configured to perform a seventh process that determines whether or not the constrained muscle length polynomial and said one or more constrained moment arm polynomials are further expandable and whether or not further expansion will be beneficial to fitting the constrained muscle length and moment arm polynomials to the input dataset; and eighth logic configured to perform an eighth process that approximates dynamics of a device based on the constrained muscle length and moment arm polynomials obtained by the sixth logic if a determination is made that the further expansion is not possible or that further expansion will not be beneficial.

20. The system of claim 19, wherein if a determination is made by the seventh process that the constrained muscle length and moment arm polynomials are further expandable and that further expansion will be beneficial, the system returns to the third process and causes the third through eighth logic to perform reiterations of the third through eighth processes, respectively.

21. The system of claim 19, wherein the third process comprises:

generating at least a first list of potential candidates for expanding the first muscle length polynomial by at least one additional term and generating a second list for expanding the first moment arm polynomial by at least one additional term;

selecting a first candidate from the first list for expanding the first muscle length polynomial and selecting a second candidate from the second list for expanding the first moment arm polynomial; and expanding the first muscle length polynomial by the first candidate and expanding the first moment arm polynomial by the second candidate.

22. The system of claim 21, wherein during the third process, selecting the first candidate from the first list for expanding the first muscle length polynomial by at least one additional term comprises:
    analyzing all of the potential candidates on the first list to determine which of the potential candidates on the first list results in a greatest improvement in fitting the first muscle length polynomial to the input dataset.

23. The system of claim 21, wherein during the third process, selecting the second candidate from the second list for expanding said at least a first moment arm polynomial by at least one additional term comprises:
    analyzing all of the potential candidates on the second list to determine which of the potential candidates on the second list results in a greatest improvement in fitting the expanded first moment arm polynomial to the input dataset.

24. The system of claim 23, wherein an Akaike information criterion (AIC) is calculated for the input dataset and used in the analysis of the third process that determines which of the potential candidates on the first and second lists result in the greatest improvement in fitting the expanded muscle length polynomial and the expanded first moment arm polynomial, respectively, to the input dataset.

\* \* \* \* \*